(12) United States Patent
Sampson

(10) Patent No.: US 9,695,440 B2
(45) Date of Patent: Jul. 4, 2017

(54) AXMI232, AXMI233, AND AXMI249 TOXIN GENES AND METHODS FOR THEIR USE

(75) Inventor: Kimberly Sampson, Durham, NC (US)

(73) Assignee: Athenix Corp., Morrisville, NC (US)

( * ) Notice: Subject to any disclaimer, the term of this patent is extended or adjusted under 35 U.S.C. 154(b) by 650 days.

(21) Appl. No.: 14/007,686

(22) PCT Filed: Mar. 29, 2012

(86) PCT No.: PCT/US2012/031214
§ 371 (c)(1),
(2), (4) Date: Dec. 13, 2013

(87) PCT Pub. No.: WO2012/135501
PCT Pub. Date: Oct. 4, 2012

(65) Prior Publication Data
US 2014/0096281 A1    Apr. 3, 2014

Related U.S. Application Data

(60) Provisional application No. 61/469,312, filed on Mar. 30, 2011.

(51) Int. Cl.
*C12N 15/82*    (2006.01)
*C07K 14/325*    (2006.01)
*A01N 63/02*    (2006.01)

(52) U.S. Cl.
CPC ......... *C12N 15/8286* (2013.01); *A01N 63/02* (2013.01); *C07K 14/325* (2013.01); *C12N 15/8261* (2013.01)

(58) Field of Classification Search
None
See application file for complete search history.

(56) References Cited

U.S. PATENT DOCUMENTS

| | | | | |
|---|---|---|---|---|
| 6,156,308 A | * | 12/2000 | Liu | C07K 14/325 424/93.2 |
| 8,759,619 B2 | * | 6/2014 | Sampson | A01N 37/46 435/252.3 |
| 2011/0203014 A1 | * | 8/2011 | Sampson | A01N 37/46 800/279 |

OTHER PUBLICATIONS

Saraswathy et al, 2004, Elect. J. Biotechnol. 7:180-190.*
Palma et al, 2014, Toxins 6:3296-3325.*
De Maagd et al, 1999, Appl. Environ. Microbiol. 65:4369-4374.*
Tounsi et al, 2003, J. Appl. Microbiol. 95:23-28.*
Aaronson et al, 2001, FEMS Microbiol. Lett. 195:1-8.*
De Maagd et al, 2001, Trends Genet. 17:193-199.*
Guo et al (2004, Proc. Natl. Acad. Sci. USA 101: 9205-9210).*

* cited by examiner

*Primary Examiner* — Anne Kubelik

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:4-19, or the nucleotide sequence set forth in SEQ ID NO: 1-3, as well as variants and fragments thereof.

23 Claims, No Drawings

AXMI232, AXMI233, AND AXMI249 TOXIN GENES AND METHODS FOR THEIR USE

CROSS REFERENCE TO RELATED APPLICATIONS

This application is a §371 U.S. National Stage of International Application No. PCT/US2012/031214, filed Mar. 29, 2012, which claims the benefit of U.S. Provisional Application Ser. No. 61/469,312, filed Mar. 30, 2011, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "SEQLIST1.txt", created on Mar. 27, 2012, and having a size of 130 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated nucleic acid molecules are provided that encode a pesticidal protein. Additionally, amino acid sequences corresponding to the pesticidal protein are encompassed. In particular, the present invention provides for an isolated or recombinant nucleic acid molecule comprising a nucleotide sequence encoding the amino acid sequence shown in SEQ ID NO:4-19 or a nucleotide sequence set forth in SEQ ID NO:1-3, as well as biologically-active variants and fragments thereof. Nucleotide sequences that are complementary to a nucleotide sequence of the invention, or that hybridize to a sequence of the invention or a complement thereof are also encompassed. Further provided are vectors, host cells, plants, and seeds comprising the nucleotide sequences of the invention, or nucleotide sequences encoding the amino acid sequences of the invention, as well as biologically-active variants and fragments thereof.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Cry1, Cry2, and Cry9 families of endotoxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Dipiera, and Coleoplera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Pesticidal proteins encompass delta-endotoxins. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Thus, provided herein are novel isolated or recombinant nucleotide sequences that confer pesticidal activity. These nucleotide sequences encode polypeptides with homology to known delta-endotoxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1-3, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in SEQ ID NO:4-19.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:4-19. In some embodiments, the fragments encompassed herein result from the removal of the C-terminal crystallization domain, e.g., by proteolysis or by insertion of a stop codon in the coding sequence. See, for example, the truncated amino acid sequences set forth in SEQ ID NO:5, 7, 10, 11, 13, 17, 18, or 19. It will be understood that the truncation site may vary by 1, 2, 3, 4, 5, 6, 7, 8, 9, 10, 11, 12, 13, 14, 15, or more amino acids on either side of the truncation site represented by the terminus of SEQ ID NO:5, 7, 10, 11, 13, 17, 18, or 19 (compared to the corresponding full-length sequence).

Preferred pesticidal proteins of the present invention are encoded by a nucleotide sequence sufficiently identical to the nucleotide sequence of SEQ ID NO: 1-3, or the pesticidal proteins are sufficiently identical to the amino acid sequence set forth in SEQ ID NO:4-19. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-19). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif. USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as nP, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Thus, the present invention encompasses probes for hybridization, as well as nucleotide sequences capable of hybridization to all or a portion of a nucleotide sequence of the invention (e.g., at least about 300 nucleotides, at least about 400, at least about 500, 1000, 1200, 1500, 2000, 2500, 3000, 3500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC 3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:4-19. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:4-19, and that exhibit pesticidal activity. A biologically active portion of a pesticidal protein can be a polypeptide that is, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:4-19. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:4-19. Variants also include polypeptides encoded by a nucleic acid molecule that hybridizes to the nucleic acid molecule of SEQ ID NO: 1-3, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

In various embodiments of the present invention, pesticidal proteins include amino acid sequences deduced from the full-length nucleotide sequences disclosed herein, and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an alternate start site for the AXMI233 protein set forth in SEQ ID NO:8, 9, 10, or 11, or an alternate start site for the AXMI249 protein set forth in SEQ ID NO:14, 15, 16, 17, 18, or 19.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:4-19, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438: Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

In various embodiments, the nucleotide sequence of the invention is operably linked to a promoter, e.g., a plant promoter. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual.* Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoplera, Diptera, Hymenoplera, Lepidoptera, Mallophaga, Homoptera, Hemiptera, Orthroptera, Thysanoptera, Dermaptera, Isoptera, Anoplura, Siphonaptera, Trichopiera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Eilaeroidea, Dascilloidea, Dryopoidea, Byrrhoidea, Cucujoidea, Meloidea, Mordelloidea, Tenebrionoidea, Bostrichoidea, Scarabaeoldea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Siaphylinidae. Superfamily Cantharoidea includes the families Cantharidae and Lampyridae. Superfamily Cleroidea includes the families Cleridae and Dermestidae. Superfamily Elateroidea includes the families Elateridae and Bupreslidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliildae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephrilidae, Agromyzidae, and Drosophilidae. Section Calyptratae includes the families Hipposcidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Salyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer, *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer, *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucoplerus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafininer; *Anaphothrips obscrurus*, grass thrips; *Solenopsis milesta*, thief ant; *Tetranychus urticae*, twospotted spider mite; *Sorghum: Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunclata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper, *Melanoplus diferentialis*, differential grasshopper; *Melanoplus sanguinipes*, migratory grasshopper, *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle;

*Bothyrus gibbosus*, carrot beetle; *Neolasioplera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper, *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus uricae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer, *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper, *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrolis ipsilon*, black cutworm; *Schizaphis graminum*, greenbug; *Blissus leucopterus leucoplerus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluoroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Funicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin. Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2 (5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad, Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2, 2-difluorethyl)amino]furan-2(5H)-on.

The following examples are offered by way of illustration and not by way of limitation.

EXPERIMENTAL EXAMPLES

Example 1. Discovery of Novel Pesticidal Genes from *Bacillus thuringiensis*

Novel pesticidal genes were identified from bacterial strains ATX38730 and ATX29611 using the following steps:
  Preparation of extrachromosomal DNA from the strain. Extrachromosomal DNA contains a mixture of some or all of the following: plasmids of various size; phage chromosomes; genomic DNA fragments not separated by the purification protocol; other uncharacterized extrachromosomal molecules.
  Mechanical or enzymatic shearing of the extrachromosomal DNA to generate size-distributed fragments.
  Sequencing of the fragmented DNA by high-throughput pyrosequencing methods.
  Identification of putative toxin genes via homology and/or other computational analyses.

When required, sequence finishing of the gene of interest by one of several PCR or cloning strategies (e.g. TAIL-PCR).

Strains ATX38730 and ATX29611 were isolated from environmental samples collected in the United States.

TABLE 1

Novel genes identified from strains ATX38730 and ATX29611

| Gene name | Molecular Weight (kD) | Closest homolog | Nucleotide SEQ ID NO | Amino acid SEQ ID NO |
|---|---|---|---|---|
| Axmi232 | 141.7 | 83.7% Cry32Ca | 1 | 4 |
| Axmi232 (truncated) | | 85.9% Cry32Ca_trun | | 5 |
| Axmi233 | 143.4 | 53.2% Cry32Da | 2 | 6 |
| Axmi233 (truncated) | | 34.4% Cry32Da_trun | | 7 |
| Axmi249 | 153.4 | 56.3% Axmi103 | 3 | 12 |
| | | 49.8% Cry32Da | | |
| Axmi249 (trun) | | 49.9% Axmi230 | | 13 |
| | | 36.6% Cry32Aa | | |

The toxin gene disclosed herein is amplified by PCR from pAX980, and the PCR product is cloned into the Bacillus expression vector pAX916, or another suitable vector, by methods well known in the art. The resulting Bacillus strain, containing the vector with axmi gene is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared and tested for activity in bioassays.

Example 2. Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) Pesticide bioassays with arthropods, CRC, Boca Raton, Fla. Alternatively, assays are commonly described in the journals *Arthropod Management Tests and Journal of Economic Entomology* or by discussion with members of the Entomological Society of America (ESA).

In some embodiments, the DNA regions encoding the toxin region of the pesticidal proteins disclosed herein are cloned into the *E. coli* expression vector pMAL-C4× behind the malE gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE Example 3. Expression and Purification Full-length or truncated versions of some genes were cloned into an *E. coli* expression vector pMAL-C4× behind the malE gene coding for Maltose binding protein (MBP) as shown in Table 2. These in-frame fusions resulted in MBP-AXMI fusion proteins expression in *E. coli*. Expression of the resulting fusion protein was induced by IPTG. Protein was then purified through a maltose column and cleaved with protease Factor Xa or trypsin to generate the untagged, purified protein. Cleavage and solubility of the proteins was determined by SDS-PAGE.

TABLE 2

Axmi constructs

| gene | construct name | backbone vector | SEQ ID NO: of protein encoded by construct |
|---|---|---|---|
| Axmi233(trun) | pAX6899 | pMAL | 7 |
| Axmi249(altstart) | pAX7708 | pMAL | 14 |

Feeding of the purified protein to Diamondback moth insects resulted in a uniform stunt and 100% mortality.

Example 4. Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:20) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 5. Transformation of Maize Cells with the Pesticidal Protein Genes Described Herein Maize ears are best collected 8-12 days after pollination. Embryos are isolated from the cars, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 6. Transformation of Genes of the Invention in Plant Cells by *Agrobacterium*-Mediated Transformation Ears are best collected 8-12 days after pollination. Embryos are isolated from the cars, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A construct comprising a heterologous promoter operably linked to a nucleic acid encoding an amino acid sequence having pesticidal activity, wherein said nucleic acid molecule is a nucleotide sequence encoding an amino acid sequence having pesticidal activity against a lepidopteran pest, wherein said nucleotide sequence is selected from the group consisting of:
   a) the nucleotide sequence set forth in SEQ ID NO:3; and
   b) a nucleotide sequence that encodes a polypeptide comprising the amino acid sequence of SEQ ID NO:12-19.

2. The construct of claim 1, wherein said nucleotide sequence is a synthetic sequence that has been designed for expression in a plant.

3. The construct of claim 1, wherein said nucleotide sequence is operably linked to a promoter capable of directing expression of said nucleotide sequence in a plant cell.

4. A vector comprising the construct of claim 1.

5. The vector of claim 4, further comprising a nucleic acid molecule encoding a heterologous polypeptide.

6. A host cell that contains the construct of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A recombinant polypeptide with pesticidal activity against a lepidopteran pest, wherein the polypeptide comprises a heterologous leader sequence or a transit peptide operably linked to a polypeptide comprising the amino acid sequence of SEQ ID NO:12-19.

13. A composition comprising the polypeptide of claim 12.

14. The composition of claim 13, wherein said composition is selected from the group consisting of a powder, dust, pellet, granule, spray, emulsion, colloid, and solution.

15. The composition of claim 13, wherein said composition is prepared by desiccation, lyophilization, homogenization, extraction, filtration, centrifugation, sedimentation, or concentration of a culture of bacterial cells.

16. The composition of claim 13, comprising from about 1% to about 99% by weight of said polypeptide.

17. A method for controlling a lepidopteran pest population, said method comprising contacting said population with a pesticidally-effective amount of the polypeptide of claim 12.

18. A method for killing a lepidopteran pest, said method comprising contacting said pest with, or feeding to said pest, a pesticidally-effective amount of the polypeptide of claim 12.

19. A method for producing a polypeptide with pesticidal activity, said method comprising culturing the host cell of claim 6 under conditions in which the nucleic acid molecule encoding the polypeptide is expressed.

20. A plant having stably incorporated into its genome a DNA construct comprising a nucleotide sequence that encodes a protein having pesticidal activity against a lepidopteran pest, wherein said nucleotide sequence is selected from the group consisting of:
   a) the nucleotide sequence set forth in SEQ ID NO:3; and
   b) a nucleotide sequence that encodes a polypeptide comprising the amino acid sequence of SEQ ID NO:12-19.

21. The plant of claim 20, wherein said plant is a plant cell.

22. A method for protecting a plant from a lepidopteran pest, said method comprising expressing in a plant or cell thereof a nucleotide sequence that encodes a polypeptide having pesticidal activity against a lepidopteran pest, wherein said nucleotide sequence is selected from the group consisting of:
   a) the nucleotide sequence set forth in SEQ ID NO:3; and
   b) a nucleotide sequence that encodes a polypeptide comprising the amino acid sequence of SEQ ID NO:12-19.

23. A method for increasing yield in a plant, said method comprising growing in a field a plant of or a seed thereof having stably incorporated into its genome a DNA construct comprising a nucleotide sequence that encodes a protein having pesticidal activity against a lepidopteran pest, wherein said nucleotide sequence is selected from the group consisting of:
   a) the nucleotide sequence set forth in SEQ ID NO:3; and
   b) a nucleotide sequence that encodes a polypeptide comprising the amino acid sequence of SEQ ID NO:12-19; wherein said field is infested with a pest against which said polypeptide has pesticidal activity and wherein the yield is increased relative to the yield of a plant not expressing said nucleotide sequence.

* * * * *

SEQUENCE LISTING

<160> NUMBER OF SEQ ID NOS: 20

<210> SEQ ID NO 1
<211> LENGTH: 3750
<212> TYPE: DNA
<213> ORGANISM: Bacillus thuringiensis

<400> SEQUENCE: 1

```
atgaatcaga attacaatga atatgaaatt ctaggtacta gtggtatggg ctatcagtca     60
agatatccac ttgcgaaaga accaggttca gaattgcaac aaatgagtta taaggattgg    120
atggataggt gtgaacgagg gtcgctggca atcacattta aatccgttat tacaaccgct    180
ttagatatta cgtctgcaat cctcgatgcg gcaaaatctc caaaagctaa agtagcaaga    240
gctgcggttc aagtccttaa tgctgttatt aaattgctgt ggcctgaacc agagaaacct    300
tctgaaccag catacgatat agatttcata tggaaagagc tgatagagag agtcgaaata    360
ctgattgaag aaaaaattga ccaagaagct tataacgccg caattggaag attatcagga    420
ttaaagagag ctttaaattt atatcaaata tcgtttgagc tttgggttga agatgaaaat    480
gaccctgagt tacaggatga tatacgaact cggtttacgt ctgcactgtt tgaacttgtg    540
actacaattg aaacatttaa atacaaagga caagagttaa atttactgac agtttttgta    600
caagctgcag attttcactt aatgttatta caacaagggg taatgtatgg agttcgttgg    660
ggactcgatc agagaacggt agattcttat tatcaaaatg acaaaggaga aggtttaaaa    720
aatttgctac cggagtattc tgattatgcc acatattggt atggcgaagg tttgaataaa    780
gcaaaaaact tgaaggcaaa tttatcagat acagtaagat atccttgggc cgcaaactta    840
gaagatgcga gtgtattaca agagctagag gattggaacc tatataacga ttatcgaaga    900
gacatgacaa tcttagtatt agatttggtt gcagtatggc caacatatga tctccattat    960
tacgataatg gaaactatgg ggtacagtct gaactgacac gatctatata ctctcaagca   1020
gtaggaaatg taatgggaac tgtatttaca aaagagcaat acgaggttag cttcgttcgc   1080
ccaccacact tagttacatg gttagaagaa atgtttgttc atataagaga caaagaacag   1140
ggggcaccta tcgaagcgga aatggctggt ataagtctag attattctta ttcaggttgg   1200
gataatacgg tttatgacat acttcaagga tatccggcga ctgggggtag tcaaattcgt   1260
gtgcttgcaa aagtaacgt gatcattcaa gatcaagaga aaaatcgagc gatttacaat    1320
acagatatcc aacatgataa actagtagat cgatttgttt tttatcaaaa tagtggagaa   1380
gttaactatg ctggtagaga taatccttca agctataaaa catttgcatg ggataccgac   1440
gttaccaact atagtagtca aatgacatgg ataaatggac cagtaaatga aggccacttt   1500
ggttatattc aggcttatgc gccggaatgg attcctgtaa gttgtgagcc ttttaataag   1560
atagtggacg cggaagatgt gattacccaa ataccagcag tgaaagctcg agaattacga   1620
tacggtgcac gcgttattaa aggacctggt agtacaggtg gagatcttgt atctattgca   1680
ccaaatggtt tgtgtgagtt gtacgtatcg tttccaaatg tgtaccgaat gtatcaggta   1740
cggatacatt atgcatgtaa agatcagacc caaataaacc taaacatagg gggcacaagt   1800
```

```
cttgacattg aacttcaacc tacgtattcg ggagtgcaat taacatatga ttcgtttgat    1860
tatgcaacaa gtaaatatag ctatatattt tatcctgact tttatgatgt ggcacagata    1920
gtaagtttgg gaaatgattt tgggacaaca cagcaagata ttatcattga taaaattgaa    1980
tttattccag ttaatatctt ctatgaagta gaacaagatc tagaaaaagc acgaaaggcc    2040
gtgaatgcct tgtttacgag tgatgcgaaa atgtcttac aattgaatgg cacagattat    2100
gcggtagacc aagctgccaa tctggtagag tgtgtatcgg atgaattcca tgctcaagaa    2160
aaaatgatcc tactggatca agtgaaagtg gcaaaacgac tgagtcgagc acgaaatcta    2220
ttaaactatg gagactttga atcgccagat tggtctggag agaatggatg gaaaacaagc    2280
cagcatgtcc acgtcgcgtc taataatcca atctttaaag gacgctatct tcacatgcca    2340
ggtgcgacaa gctcacagtt ctctaacaat gtctatccaa catatgtcta tcaaaaggtg    2400
gatgaatcga attaaaaatc ctatacacgt tacctggtac gcggatttgt cggaaatagt    2460
aaggacctag aattactggt tgaacgatat ggaaaagacg tacatgtaga actagatgta    2520
ccaaatgaca ttcaatattc tttaccgatg aatgaatgcg gcgaatttga tcgatgccga    2580
cctgtatcgt ataaagcagg gtcccatcac acatgtacat gtaaggatac cgcttccctg    2640
tatacggatt gtcagtgtaa agacaaggtg aatcgtcctt cggccgacgt atatacaaat    2700
ataccgacag gtagtgcggg atatgcgaat ggattccatg cccataaatc ctgtggatgt    2760
aagaacaacg atatatatca gaaggaaaca catccgcata agtcttgtgg atgcaaagac    2820
ccacatgtct tctcatacca tattgataca ggatgtgtgg atcaagaaga aaaccttggt    2880
ttgtggttcg cattaaaaat tgcgagcgaa aaaggtgtcg cgaacatcga caacctggaa    2940
atcattgagg cacaaccact tacaggggaa gcattagcac gtgtgaaaaa acgcgaacag    3000
aaatggaaac acgaaatggt aaacagacgg ttagaaacag aaaaagctgt acaagcagcg    3060
caaggtgcga ttcagcccct cttcacaaac gcgcagtaca atcgtttaca atttgaaacg    3120
ctgttcccgc aaattgtccg tgcagagtgg cttgtacaac agattccata tgtacatcac    3180
ccattcttga gcaagcact tccagctgta ccaggcatga attttgaaat cgcccaacac    3240
ttattggcag tgatcagaaa tgcccatgcc ttatatgaag gacggaatct cgtgcgtaat    3300
ggtacgttca gctctggtac aggaagctgg catgtgtcag aaggcgtaaa ggtgcagcca    3360
ctgcaaaaca cttctgtact cgttctatcg gaatggaatc atgaagcgtc ccagcagtta    3420
cgtatcgatc cagatcgtgg gtatgtgtta cgtgtaacag cccgaaaaga gggtcctgga    3480
aaaggtacgg tgacgatgag tgactgcgca gcatatacag agacactgac ctttacatct    3540
tgtgactata atacgattgg ctcccaaata atgacgggtg gtacgttatc tggatttgtg    3600
acaaagacgc tagaaatctt cccagacaca gattgtattc ggatcgatat tggtgagaca    3660
gaaggtacgt ttaagattga aagtgtagaa ttgatttgta tggaacaaat ggaaaaccat    3720
ttatatgata tggcgggaa tttagaagaa                                      3750
```

<210> SEQ ID NO 2
<211> LENGTH: 3828
<212> TYPE: DNA
<213> ORGANISM: Bacillus thuringiensis

<400> SEQUENCE: 2

```
atgaagcaaa attccaatga tgaatatgaa atattggata gtaaaggtat gcacgatccg     60
tataagaaat tccctattca tcacacaagt tcacctagct ttgattttaa aatgggaaga    120
```

```
caaaaagaaa tagatacact ttctttgata ccagaggaaa taagcccatt attcaacccc      180
gcagctatta taacggctgc taaagttctt tttaatattg gatcaaaaat agcatctgga      240
aaaagattct tggattcagt attagccata ttatggcctg aggctgctgc tcaaagtaaa      300
tgggaagaat ttattgctct tgcagaacaa ttgattcaag aaaaaattgc agaatatgca      360
agaggtgcag ccattgcgaa attaatagga ttaaaagacg ttatgatggt gtacgaaggt      420
gcttttgctg attgggaaaa gaatcaaacc gatccccaaa aacaggaggc tgtacgaaat      480
gagtttcgaa atgctaatga tattattgta gcagctatgc cagaattcgc tattaaaaat      540
tatgaaattc aacttttaac tgtgtatgca gaagcagcaa atttacattt aacattatta      600
cgagatgctt caatttatgg attacaatgg ggaatgggac aatcagaagt ggataggcac      660
tatacagctc aaatgtctag aacacaaaca tatacagatt attgcgtgag ttggtatgat      720
attggtttag aaaaagctaa aaagctaaag gcaaacatat atgatagaga tcaatatcct      780
tggattggtg cagggcctcc acctggttat ccaatgtcaa tattccaaac aacagaagac      840
tggaatttat ttaataactt cagaagagat atgacgctac aggtattaga tttggttgct      900
tattggccca catatgatgt taaaaaatat cctatttcaa cgcaagtgca acttactcga      960
gatatatata caaatatatg ggggatagac aacactagtg tagataaaat agaagcacaa     1020
tttgtcagac ctccacattt ggtcacgcac ttagatgcac tggatttcta cgtagactac     1080
aacctacatt ttaacggttc cgaaaatatc atgggtgaac gtaaggttta caactacact     1140
agtgagcgcg aaatagaaag tcctatatca ggtaagcaaa cacaaaacaa aaagacactt     1200
acagtacgag gaaacccagc taatacgatt cgttgttggc actatgtaga ggcctccatt     1260
ttagatttcc ctggcagact tagaattgga aatgttgtat ctggatgggg cggagcatgg     1320
tcaacggccg aaattcctga taaccatata tcttggataa ccacaacttt ccccactcct     1380
tctttagtaa taaaaggtat gagagcagtt ggatttagtt ggatgtctaa tactgtggat     1440
ccaactaaca cagtagcccc aggcagaatt actcaaattc cggctgtgaa ggctagagat     1500
attggtcctg gtggaagggt cataaagggg ccggggacga ccggaggaga cttagtagaa     1560
ttaaatgcgg cattaactac aggcatctca ttaaatatatt catcaccaca aaatgaagta     1620
tacaccatga gaattcgtta tgcgagtaga gggaacggac aattaagatt aacaacttat     1680
caatatagtg gttatgcacc tcgtatagtt aatttttaatg caacggattc tagcggttcg     1740
ctgaaattta attctttcaa ttatctaact atcgggaatg tagctgctga tccaactgct     1800
cttcctcgtt ttgtctttga tctttattca ggatcaccta ttattattga taaaatcgaa     1860
tttcttccga ggggcataat tttagaagaa gctgaagcta accaagattt agaaaaagca     1920
agaaaggctg tgaatgcctt gtttacaaat gatgcgaaag ataatttgaa actaaacatg     1980
acggattatg caatagatca agctgcaaac ctagtggaat gtctgtcgga cgagttctgt     2040
gaccaagaaa aaatgatcct gctggatcaa gtcaagtttg cgaaacgttt gagtcaagca     2100
cgaaacctat taaactacgg agattttgaa tccccagatt ggtctggtga aaatggatgg     2160
aagacaagcc cacatgttca tgtcgcatcc gataacccaa tctttaaagg acgctatctc     2220
catatgccag gcgcaaatca accgcaaatg agtgatacgg tatatccaac gtatctctat     2280
caaaaggtag atgaatcgaa attaaaatcc tatacgcgtt accatgtacg gggatttgtt     2340
ggtaacagta aagatcttgc attactcgtg gaacgatatg gaaaagaagt tcatgtcgaa     2400
atggatgtgc caaatgatat ccgctataca ttaccgatga tgaatgcggg ggatttgat     2460
cgatgcggtc atagctctta tcaagctgga acagattctc acacatgtac atgtaaagat     2520
```

```
cctgctcaaa tggatgcggc gtgtcaatgt aaagacaaat caaaacgtac cgcatcaggt        2580
gtgtatacca acgtatatgc aggcagtgat atgatgtatc tagatggata ccatgcgcat        2640
acatcttgcg gatgcaaaga tccacacgtc ttctctttcc acattgacac aggatgtgta        2700
gatgtagaag aaaatgcagg ccttctattt gcgctgaaaa ttgcgagcac cgatggtgtg        2760
gcaaatatag ataatctcga aatcattgag ggacaacctt taacaggaga ggcattagcg        2820
cgtgtgaaaa acgagagca caaatggaaa gaagaaagga acaaaaacg ctgtaaaaca         2880
```

```
ccaggtatgc tacaactatt agcaaactat acaaatcatt gtgtacgttg gtacaatgca    840
ggtttagcaa cttttaattc atatcttcaa tggcaggaac tcaataccct tccgtagagat   900
atgaccataa tggtgctcga tattgcctca ctatggccaa cctacgatcc gaagagttat    960
cctgtcattg ccaagtcgca acttactagg gtattatata caccagcgat aggcaatgat   1020
acagattttg aaaaattact ccctcctcca tcgttattta gctggttacg tgaggcaata   1080
ttctatacgc caaacccagt gtatagaatg gagtacgtga aatatacatt agttctacaa   1140
aagactcttt ccaacgatcg ctatgaacaa acctacggtt caaactttgg ggctgacata   1200
gcttactccg taaagattgg tacggcgcct aattcggagg tttatagaat gcataccaat   1260
gctgttattt atagcaatga caatgcaagt ttggggaaaa tcacctttca cttttctcct   1320
tcaggaacct ctgagtctgt aggaagagaa atagtaggaa ctggtattga tcaaggattt   1380
gcgtgtaggt cgaatctgaa tgaaccctgt gatccttgtg tgactgcttg tgaagttggt   1440
tctgtgaatg ctagcctccc ttgtgatagt ccaagtcttt atagtgagcg attgtcgtgg   1500
attagcgggg agattttacg cagtgtaaat ttttctgcat tgaataatat tgcctatggc   1560
tggacacatg taagcgcaga tgccaataac ctgataagtg ctgaacagat tacccaaatt   1620
ccagcagtga aggcatatga attaagtgga gatgctcttg ttataaaggg ccctggtagt   1680
acagggggag atttagtaca actttctagt ggagctgaaa ctggacaaat ggctatgtgg   1740
ataaccacac cacaggggaag ccatcgttat cgtgtaagaa tacgttatgc aagtagtatg   1800
cagacaaatt tagaaatctt tatgacaggg gctttcggag agtttagtgc tccagctact   1860
acaactgata cgacaaatct cacatatgat aaatttggat acctagaaac cgttttgtat   1920
tcttatgctc atgttgaaga aagtaccgaa cacatacgaa tgtatgctac cggatcagga   1980
tcaggttcgt ttatcttaga taaaatcgaa tttattccaa ttgaaggatc actggaagcc   2040
tatcaagcgg accaagatgt agaaaaagca agaaaggcag tgaacgcctt gtttacaggt   2100
gatgcgaaaa atgccctgaa attgaatgtg acggattatg cagtagatca agcggctaat   2160
cttgtcgagt gtgtatcgga agacttccat gcacaagaaa aaatgatcct tctggatcaa   2220
gtcaagcttg cgaaacgact cagtcaagca cgaaatctat aaactatgg agattttgaa    2280
tctccagatt ggtctggtga aatggatgg aagacaagtc cacatgttca tgtcgcatcc    2340
gacaatccaa tctttaaagg acattatctt catatgccag gcgcgaatca accgcaaatg   2400
agtgatacga tatccaac gtacatctat caaaaagtag atgaatcgaa attaaaatct    2460
tatacgcgtt accatgtacg gggatttgtt ggtaacagta aaaatcttga attattcgtg   2520
gaacgatatg gaaaagaagt ccatgtcgaa atggatgtgc caaatgatat ccgctataca   2580
ttaccgatga atgaatgcgg tggatttgat cgatgtggtc atagctctta tcaagctgga   2640
acagattctc gcacatgtac atgtaaagat acggctcgaa tggatgcgga atgtcaatgt   2700
aaagaccaac caaaacgcac cgcatcgggt gtatatacaa acgcatatgc aggtaatgat   2760
aggatgtatc cggatgggta ccatgcacac aaatcgtgtg gatgtaacaa aaaaggtgga   2820
tatccaaatg gaaaacatgc gcataaatct tgcggatgca agatccacac cgtcttctct   2880
ttccacattg acacaggatg tgtagatgta aagaaaatg caggccttct atttgcactg    2940
aaaattgcga gcaccgatgg tctagcaaat atagataatc tcgaaatcat tgagggacaa   3000
cctttaacag gagaggcatt ggcacgtgtg aaaaaacgag agcacagatg gaaagaagaa   3060
atgaaacaaa aacgctgtaa aacaaaagaa actgtagagg cggccctaac agctatcaat   3120
gccttattca caaacaaaca atacaatcgc ttaaaatttg atacgttgtt cccgcacatt   3180
```

```
cttcatacgg atgaacttgt acaacgtatc ccatatgtgt atcacccatt tttacaggat    3240
gcatacccgg atgtaccagg aatgaactat gctattttcc aacaactctc ttccatgatt    3300
aatcgagcac gtgggttata tgacatgcgg aatcttgtac aaaatggaac cttcagtagt    3360
ggcgcaggca gttggcatgt gacagatggt gtaaatacgc aaccagaagg aaatacatct    3420
gtactcgttt acgtgagtg gagtgataaa gcagtccaaa acttgcgaat cgatgaagaa    3480
cgcgggtatg tgttacgtgt aacggcacga aagaaggaa acggcgacgg atatgtggtg    3540
atccatgatt gcgacaacca aatggagaag ttgacattta cagcgtgtga ttattctaca    3600
acgagggcaa gtacgggtac acaagcaaca gtcataccag ttacaaactg cccgccatgt    3660
cacagcggga catggggaga agagaggcca acgccaatta cgatgttaac gggatatgtc    3720
acaaaaacag cggaaatctt cccagatacc gatcgtatcc gcattgaaat cggagaaaca    3780
gaaggaacat tcaaaatcga aagtgtggaa ctcatctgca tggagcatat ggaagaccat    3840
atgtatgata tggccggaaa cttagaagaa gaaatgcagg gtctaggaat agagagttct    3900
catgcagtga cgcatgagat gtgcttctca tgggatatta tgtgtccgat ggaagcaagc    3960
ataccaccga ttgtgccgcc tactaatatg tatgatatgg cagggaatgt ggaggaagaa    4020
atgaaatatc tgaagccatc ttctatggct agtacattag atccgatatg ttacacaaag    4080
attggagaat tggttgtcc cttaaatcaa                                      4110

<210> SEQ ID NO 4
<211> LENGTH: 1250
<212> TYPE: PRT
<213> ORGANISM: Bacillus thuringiensis

<400> SEQUENCE: 4

Met Asn Gln Asn Tyr Asn Glu Tyr Glu Ile Leu Gly Thr Ser Gly Met
1               5                   10                  15

Gly Tyr Gln Ser Arg Tyr Pro Leu Ala Lys Glu Pro Gly Ser Glu Leu
            20                  25                  30

Gln Gln Met Ser Tyr Lys Asp Trp Met Asp Arg Cys Glu Arg Gly Ser
        35                  40                  45

Leu Ala Ile Thr Phe Lys Ser Val Ile Thr Thr Ala Leu Asp Ile Thr
    50                  55                  60

Ser Ala Ile Leu Asp Ala Ala Lys Ser Pro Lys Ala Lys Val Ala Arg
65                  70                  75                  80

Ala Ala Val Gln Val Leu Asn Ala Val Ile Lys Leu Leu Trp Pro Glu
                85                  90                  95

Pro Glu Lys Pro Ser Glu Pro Ala Tyr Asp Ile Asp Phe Ile Trp Lys
            100                 105                 110

Glu Leu Ile Glu Arg Val Glu Ile Leu Ile Glu Lys Ile Asp Gln
        115                 120                 125

Glu Ala Tyr Asn Ala Ala Ile Gly Arg Leu Ser Gly Leu Lys Arg Ala
    130                 135                 140

Leu Asn Leu Tyr Gln Ile Ser Phe Glu Leu Trp Val Glu Asp Glu Asn
145                 150                 155                 160

Asp Pro Glu Leu Gln Asp Asp Ile Arg Thr Arg Phe Thr Ser Ala Leu
                165                 170                 175

Phe Glu Leu Val Thr Thr Ile Glu Thr Phe Lys Tyr Lys Gly Gln Glu
            180                 185                 190

Leu Asn Leu Leu Thr Val Phe Val Gln Ala Ala Asp Phe His Leu Met
        195                 200                 205
```

```
Leu Leu Gln Gln Gly Val Met Tyr Gly Val Arg Trp Gly Leu Asp Gln
        210                 215                 220

Arg Thr Val Asp Ser Tyr Tyr Gln Asn Asp Lys Gly Glu Gly Leu Lys
225                 230                 235                 240

Asn Leu Leu Pro Glu Tyr Ser Asp Tyr Ala Thr Tyr Trp Tyr Gly Glu
            245                 250                 255

Gly Leu Asn Lys Ala Lys Asn Leu Lys Ala Asn Leu Ser Asp Thr Val
        260                 265                 270

Arg Tyr Pro Trp Ala Ala Asn Leu Glu Asp Ala Ser Val Leu Gln Glu
            275                 280                 285

Leu Glu Asp Trp Asn Leu Tyr Asn Asp Tyr Arg Arg Asp Met Thr Ile
290                 295                 300

Leu Val Leu Asp Leu Val Ala Val Trp Pro Thr Tyr Asp Leu His Tyr
305                 310                 315                 320

Tyr Asp Asn Gly Asn Tyr Gly Val Gln Ser Glu Leu Thr Arg Ser Ile
            325                 330                 335

Tyr Ser Gln Ala Val Gly Asn Val Met Gly Thr Val Phe Thr Lys Glu
            340                 345                 350

Gln Tyr Glu Val Ser Phe Val Arg Pro Pro His Leu Val Thr Trp Leu
        355                 360                 365

Glu Glu Met Phe Val His Ile Arg Asp Lys Glu Gln Gly Ala Pro Ile
370                 375                 380

Glu Ala Glu Met Ala Gly Ile Ser Leu Asp Tyr Ser Tyr Ser Gly Trp
385                 390                 395                 400

Asp Asn Thr Val Tyr Asp Ile Leu Gln Gly Tyr Pro Ala Thr Gly Gly
            405                 410                 415

Ser Gln Ile Arg Val Leu Ala Lys Ser Asn Val Ile Gln Asp Gln
        420                 425                 430

Glu Lys Asn Arg Ala Ile Tyr Asn Thr Asp Ile Gln His Asp Lys Leu
        435                 440                 445

Val Asp Arg Phe Val Phe Tyr Gln Asn Ser Gly Glu Val Asn Tyr Ala
450                 455                 460

Gly Arg Asp Asn Pro Ser Ser Tyr Lys Thr Phe Ala Trp Asp Thr Asp
465                 470                 475                 480

Val Thr Asn Tyr Ser Ser Gln Met Thr Trp Ile Asn Gly Pro Val Asn
            485                 490                 495

Glu Gly His Phe Gly Tyr Ile Gln Ala Tyr Ala Pro Glu Trp Ile Pro
            500                 505                 510

Val Ser Cys Glu Pro Phe Asn Lys Ile Val Asp Ala Glu Asp Val Ile
        515                 520                 525

Thr Gln Ile Pro Ala Val Lys Ala Arg Glu Leu Arg Tyr Gly Ala Arg
        530                 535                 540

Val Ile Lys Gly Pro Gly Ser Thr Gly Gly Asp Leu Val Ser Ile Ala
545                 550                 555                 560

Pro Asn Gly Leu Cys Glu Leu Tyr Val Ser Phe Pro Asn Val Tyr Arg
            565                 570                 575

Met Tyr Gln Val Arg Ile His Tyr Ala Cys Lys Asp Gln Thr Gln Ile
            580                 585                 590

Asn Leu Asn Ile Gly Gly Thr Ser Leu Asp Ile Glu Leu Gln Pro Thr
        595                 600                 605

Tyr Ser Gly Val Gln Leu Thr Tyr Asp Ser Phe Asp Tyr Ala Thr Ser
610                 615                 620
```

```
Lys Tyr Ser Tyr Ile Phe Tyr Pro Asp Phe Tyr Asp Val Ala Gln Ile
625                 630                 635                 640

Val Ser Leu Gly Asn Asp Phe Gly Thr Thr Gln Gln Asp Ile Ile Ile
                645                 650                 655

Asp Lys Ile Glu Phe Ile Pro Val Asn Ile Phe Tyr Glu Val Glu Gln
            660                 665                 670

Asp Leu Glu Lys Ala Arg Lys Ala Val Asn Ala Leu Phe Thr Ser Asp
        675                 680                 685

Ala Lys Asn Val Leu Gln Leu Asn Gly Thr Asp Tyr Ala Val Asp Gln
    690                 695                 700

Ala Ala Asn Leu Val Glu Cys Val Ser Asp Glu Phe His Ala Gln Glu
705                 710                 715                 720

Lys Met Ile Leu Leu Asp Gln Val Lys Val Ala Lys Arg Leu Ser Arg
                725                 730                 735

Ala Arg Asn Leu Leu Asn Tyr Gly Asp Phe Glu Ser Pro Asp Trp Ser
            740                 745                 750

Gly Glu Asn Gly Trp Lys Thr Ser Gln His Val His Val Ala Ser Asn
        755                 760                 765

Asn Pro Ile Phe Lys Gly Arg Tyr Leu His Met Pro Gly Ala Thr Ser
770                 775                 780

Ser Gln Phe Ser Asn Asn Val Tyr Pro Thr Tyr Val Tyr Gln Lys Val
785                 790                 795                 800

Asp Glu Ser Lys Leu Lys Ser Tyr Thr Arg Tyr Leu Val Arg Gly Phe
                805                 810                 815

Val Gly Asn Ser Lys Asp Leu Glu Leu Leu Val Glu Arg Tyr Gly Lys
            820                 825                 830

Asp Val His Val Glu Leu Asp Val Pro Asn Asp Ile Gln Tyr Ser Leu
        835                 840                 845

Pro Met Asn Glu Cys Gly Glu Phe Asp Arg Cys Arg Pro Val Ser Tyr
    850                 855                 860

Lys Ala Gly Ser His His Thr Cys Thr Cys Lys Asp Thr Ala Ser Leu
865                 870                 875                 880

Tyr Thr Asp Cys Gln Cys Lys Asp Lys Val Asn Arg Pro Ser Ala Asp
                885                 890                 895

Val Tyr Thr Asn Ile Pro Thr Gly Ser Ala Gly Tyr Ala Asn Gly Phe
            900                 905                 910

His Ala His Lys Ser Cys Gly Cys Lys Asn Asn Asp Ile Tyr Gln Lys
        915                 920                 925

Glu Thr His Pro His Lys Ser Cys Gly Cys Lys Asp Pro His Val Phe
    930                 935                 940

Ser Tyr His Ile Asp Thr Gly Cys Val Asp Gln Glu Glu Asn Leu Gly
945                 950                 955                 960

Leu Trp Phe Ala Leu Lys Ile Ala Ser Glu Lys Gly Val Ala Asn Ile
                965                 970                 975

Asp Asn Leu Glu Ile Ile Glu Ala Gln Pro Leu Thr Gly Glu Ala Leu
            980                 985                 990

Ala Arg Val Lys Lys Arg Glu Gln Lys Trp Lys His Glu Met Val Asn
        995                 1000                1005

Arg Arg Leu Glu Thr Glu Lys Ala Val Gln Ala Ala Gln Gly Ala
        1010                1015                1020

Ile Gln Pro Leu Phe Thr Asn Ala Gln Tyr Asn Arg Leu Gln Phe
        1025                1030                1035

Glu Thr Leu Phe Pro Gln Ile Val Arg Ala Glu Trp Leu Val Gln
```

```
                    1040                1045                1050
Gln Ile Pro Tyr Val His His Pro Phe Leu Ser Glu Ala Leu Pro
            1055                1060                1065

Ala Val Pro Gly Met Asn Phe Glu Ile Ala Gln His Leu Leu Ala
        1070                1075                1080

Val Ile Arg Asn Ala His Ala Leu Tyr Glu Gly Arg Asn Leu Val
    1085                1090                1095

Arg Asn Gly Thr Phe Ser Ser Gly Thr Gly Ser Trp His Val Ser
1100                1105                1110

Glu Gly Val Lys Val Gln Pro Leu Gln Asn Thr Ser Val Leu Val
    1115                1120                1125

Leu Ser Glu Trp Asn His Glu Ala Ser Gln Gln Leu Arg Ile Asp
        1130                1135                1140

Pro Asp Arg Gly Tyr Val Leu Arg Val Thr Ala Arg Lys Glu Gly
    1145                1150                1155

Pro Gly Lys Gly Thr Val Thr Met Ser Asp Cys Ala Ala Tyr Thr
    1160                1165                1170

Glu Thr Leu Thr Phe Thr Ser Cys Asp Tyr Asn Thr Ile Gly Ser
    1175                1180                1185

Gln Ile Met Thr Gly Gly Thr Leu Ser Gly Phe Val Thr Lys Thr
    1190                1195                1200

Leu Glu Ile Phe Pro Asp Thr Asp Cys Ile Arg Ile Asp Ile Gly
    1205                1210                1215

Glu Thr Glu Gly Thr Phe Lys Ile Glu Ser Val Glu Leu Ile Cys
    1220                1225                1230

Met Glu Gln Met Glu Asn His Leu Tyr Asp Met Ala Gly Asn Leu
    1235                1240                1245

Glu Glu
    1250

<210> SEQ ID NO 5
<211> LENGTH: 666
<212> TYPE: PRT
<213> ORGANISM: Bacillus thuringiensis

<400> SEQUENCE: 5

Met Asn Gln Asn Tyr Asn Glu Tyr Glu Ile Leu Gly Thr Ser Gly Met
1               5                   10                  15

Gly Tyr Gln Ser Arg Tyr Pro Leu Ala Lys Glu Pro Gly Ser Glu Leu
            20                  25                  30

Gln Gln Met Ser Tyr Lys Asp Trp Met Asp Arg Cys Glu Arg Gly Ser
        35                  40                  45

Leu Ala Ile Thr Phe Lys Ser Val Ile Thr Thr Ala Leu Asp Ile Thr
    50                  55                  60

Ser Ala Ile Leu Asp Ala Ala Lys Ser Pro Lys Ala Lys Val Ala Arg
65                  70                  75                  80

Ala Ala Val Gln Val Leu Asn Ala Val Ile Lys Leu Leu Trp Pro Glu
                85                  90                  95

Pro Glu Lys Pro Ser Glu Pro Ala Tyr Asp Ile Asp Phe Ile Trp Lys
            100                 105                 110

Glu Leu Ile Glu Arg Val Glu Ile Leu Ile Glu Glu Lys Ile Asp Gln
        115                 120                 125

Glu Ala Tyr Asn Ala Ala Ile Gly Arg Leu Ser Gly Leu Lys Arg Ala
    130                 135                 140
```

```
Leu Asn Leu Tyr Gln Ile Ser Phe Glu Leu Trp Val Glu Asp Glu Asn
145                 150                 155                 160

Asp Pro Glu Leu Gln Asp Asp Ile Arg Thr Arg Phe Thr Ser Ala Leu
                165                 170                 175

Phe Glu Leu Val Thr Thr Ile Glu Thr Phe Lys Tyr Lys Gly Gln Glu
            180                 185                 190

Leu Asn Leu Leu Thr Val Phe Val Gln Ala Ala Asp Phe His Leu Met
        195                 200                 205

Leu Leu Gln Gln Gly Val Met Tyr Gly Val Arg Trp Gly Leu Asp Gln
    210                 215                 220

Arg Thr Val Asp Ser Tyr Tyr Gln Asn Asp Lys Gly Glu Gly Leu Lys
225                 230                 235                 240

Asn Leu Leu Pro Glu Tyr Ser Asp Tyr Ala Thr Tyr Trp Tyr Gly Glu
                245                 250                 255

Gly Leu Asn Lys Ala Lys Asn Leu Lys Ala Asn Leu Ser Asp Thr Val
            260                 265                 270

Arg Tyr Pro Trp Ala Ala Asn Leu Glu Asp Ala Ser Val Leu Gln Glu
        275                 280                 285

Leu Glu Asp Trp Asn Leu Tyr Asn Asp Tyr Arg Arg Asp Met Thr Ile
    290                 295                 300

Leu Val Leu Asp Leu Val Ala Val Trp Pro Thr Tyr Asp Leu His Tyr
305                 310                 315                 320

Tyr Asp Asn Gly Asn Tyr Gly Val Gln Ser Glu Leu Thr Arg Ser Ile
                325                 330                 335

Tyr Ser Gln Ala Val Gly Asn Val Met Gly Thr Val Phe Thr Lys Glu
            340                 345                 350

Gln Tyr Glu Val Ser Phe Val Arg Pro Pro His Leu Val Thr Trp Leu
        355                 360                 365

Glu Glu Met Phe Val His Ile Arg Asp Lys Glu Gln Gly Ala Pro Ile
    370                 375                 380

Glu Ala Glu Met Ala Gly Ile Ser Leu Asp Tyr Ser Tyr Ser Gly Trp
385                 390                 395                 400

Asp Asn Thr Val Tyr Asp Ile Leu Gln Gly Tyr Pro Ala Thr Gly Gly
                405                 410                 415

Ser Gln Ile Arg Val Leu Ala Lys Ser Asn Val Ile Gln Asp Gln
            420                 425                 430

Glu Lys Asn Arg Ala Ile Tyr Asn Thr Asp Ile Gln His Asp Lys Leu
        435                 440                 445

Val Asp Arg Phe Val Phe Tyr Gln Asn Ser Gly Glu Val Asn Tyr Ala
    450                 455                 460

Gly Arg Asp Asn Pro Ser Ser Tyr Lys Thr Phe Ala Trp Asp Thr Asp
465                 470                 475                 480

Val Thr Asn Tyr Ser Ser Gln Met Thr Trp Ile Asn Gly Pro Val Asn
                485                 490                 495

Glu Gly His Phe Gly Tyr Ile Gln Ala Tyr Ala Pro Glu Trp Ile Pro
            500                 505                 510

Val Ser Cys Glu Pro Phe Asn Lys Ile Val Asp Ala Glu Asp Val Ile
        515                 520                 525

Thr Gln Ile Pro Ala Val Lys Ala Arg Glu Leu Arg Tyr Gly Ala Arg
    530                 535                 540

Val Ile Lys Gly Pro Gly Ser Thr Gly Gly Asp Leu Val Ser Ile Ala
545                 550                 555                 560

Pro Asn Gly Leu Cys Glu Leu Tyr Val Ser Phe Pro Asn Val Tyr Arg
```

-continued

```
                565                 570                 575
Met Tyr Gln Val Arg Ile His Tyr Ala Cys Lys Asp Gln Thr Gln Ile
                580                 585                 590

Asn Leu Asn Ile Gly Gly Thr Ser Leu Asp Ile Glu Leu Gln Pro Thr
                595                 600                 605

Tyr Ser Gly Val Gln Leu Thr Tyr Asp Ser Phe Asp Tyr Ala Thr Ser
        610                 615                 620

Lys Tyr Ser Tyr Ile Phe Tyr Pro Asp Phe Tyr Asp Val Ala Gln Ile
625                 630                 635                 640

Val Ser Leu Gly Asn Asp Phe Gly Thr Thr Gln Gln Asp Ile Ile
                645                 650                 655

Asp Lys Ile Glu Phe Ile Pro Val Asn Ile
                660                 665

<210> SEQ ID NO 6
<211> LENGTH: 1276
<212> TYPE: PRT
<213> ORGANISM: Bacillus thuringiensis

<400> SEQUENCE: 6

Met Lys Gln Asn Ser Asn Asp Glu Tyr Glu Ile Leu Asp Ser Lys Gly
1               5                   10                  15

Met His Asp Pro Tyr Lys Lys Phe Pro Ile His His Thr Ser Ser Pro
                20                  25                  30

Ser Phe Asp Phe Lys Met Gly Arg Gln Lys Glu Ile Asp Thr Leu Ser
        35                  40                  45

Leu Ile Pro Glu Glu Ile Ser Pro Leu Phe Asn Pro Ala Ala Ile Ile
        50                  55                  60

Thr Ala Ala Lys Val Leu Phe Asn Ile Gly Ser Lys Ile Ala Ser Gly
65              70                  75                  80

Lys Arg Phe Leu Asp Ser Val Leu Ala Ile Leu Trp Pro Glu Ala Ala
                85                  90                  95

Ala Gln Ser Lys Trp Glu Glu Phe Ile Ala Leu Ala Glu Gln Leu Ile
                100                 105                 110

Gln Glu Lys Ile Ala Glu Tyr Ala Arg Gly Ala Ala Ile Ala Lys Leu
        115                 120                 125

Ile Gly Leu Lys Asp Val Met Met Val Tyr Glu Gly Ala Phe Ala Asp
130                 135                 140

Trp Glu Lys Asn Gln Thr Asp Pro Gln Lys Gln Glu Ala Val Arg Asn
145                 150                 155                 160

Glu Phe Arg Asn Ala Asn Asp Ile Ile Val Ala Ala Met Pro Glu Phe
                165                 170                 175

Ala Ile Lys Asn Tyr Glu Ile Gln Leu Leu Thr Val Tyr Ala Glu Ala
        180                 185                 190

Ala Asn Leu His Leu Thr Leu Leu Arg Asp Ala Ser Ile Tyr Gly Leu
        195                 200                 205

Gln Trp Gly Met Gly Gln Ser Glu Val Asp Arg His Tyr Thr Ala Gln
        210                 215                 220

Met Ser Arg Thr Gln Thr Tyr Thr Asp Tyr Cys Val Ser Trp Tyr Asp
225                 230                 235                 240

Ile Gly Leu Glu Lys Ala Lys Lys Leu Lys Ala Asn Ile Tyr Asp Arg
                245                 250                 255

Asp Gln Tyr Pro Trp Ile Gly Ala Gly Pro Pro Gly Tyr Pro Met
        260                 265                 270
```

```
Ser Ile Phe Gln Thr Thr Glu Asp Trp Asn Leu Phe Asn Asn Phe Arg
            275                 280                 285

Arg Asp Met Thr Leu Gln Val Leu Asp Leu Val Ala Tyr Trp Pro Thr
        290                 295                 300

Tyr Asp Val Lys Lys Tyr Pro Ile Ser Thr Gln Val Gln Leu Thr Arg
305                 310                 315                 320

Asp Ile Tyr Thr Asn Ile Trp Gly Ile Asp Asn Thr Ser Val Asp Lys
                325                 330                 335

Ile Glu Ala Gln Phe Val Arg Pro Pro His Leu Val Thr His Leu Asp
            340                 345                 350

Ala Leu Asp Phe Tyr Val Asp Tyr Asn Leu His Phe Asn Gly Ser Glu
        355                 360                 365

Asn Ile Met Gly Glu Arg Lys Val Tyr Asn Tyr Thr Ser Glu Arg Glu
    370                 375                 380

Ile Glu Ser Pro Ile Ser Gly Lys Gln Thr Gln Asn Lys Lys Thr Leu
385                 390                 395                 400

Thr Val Arg Gly Asn Pro Ala Asn Thr Ile Arg Cys Trp His Tyr Val
                405                 410                 415

Glu Ala Ser Ile Leu Asp Phe Pro Gly Arg Leu Arg Ile Gly Asn Val
            420                 425                 430

Val Ser Gly Trp Gly Gly Ala Trp Ser Thr Ala Glu Ile Pro Asp Asn
        435                 440                 445

His Ile Ser Trp Ile Thr Thr Thr Phe Pro Thr Pro Ser Leu Val Ile
    450                 455                 460

Lys Gly Met Arg Ala Val Gly Phe Ser Trp Met Ser Asn Thr Val Asp
465                 470                 475                 480

Pro Thr Asn Thr Val Ala Pro Gly Arg Ile Thr Gln Ile Pro Ala Val
                485                 490                 495

Lys Ala Arg Asp Ile Gly Pro Gly Gly Arg Val Ile Lys Gly Pro Gly
            500                 505                 510

Thr Thr Gly Gly Asp Leu Val Glu Leu Asn Ala Ala Leu Thr Thr Gly
        515                 520                 525

Ile Ser Leu Asn Ile Ser Ser Pro Gln Asn Glu Val Tyr Thr Met Arg
    530                 535                 540

Ile Arg Tyr Ala Ser Arg Gly Asn Gly Gln Leu Arg Leu Thr Thr Tyr
545                 550                 555                 560

Gln Tyr Ser Gly Tyr Ala Pro Arg Ile Val Asn Phe Asn Ala Thr Asp
                565                 570                 575

Ser Ser Gly Ser Leu Lys Phe Asn Ser Phe Asn Tyr Leu Thr Ile Gly
            580                 585                 590

Asn Val Ala Ala Asp Pro Thr Ala Leu Pro Arg Phe Val Phe Asp Leu
        595                 600                 605

Tyr Ser Gly Ser Pro Ile Ile Ile Asp Lys Ile Glu Phe Leu Pro Arg
    610                 615                 620

Gly Ile Ile Leu Glu Glu Ala Glu Ala Asn Gln Asp Leu Glu Lys Ala
625                 630                 635                 640

Arg Lys Ala Val Asn Ala Leu Phe Thr Asn Asp Ala Lys Asp Asn Leu
                645                 650                 655

Lys Leu Asn Met Thr Asp Tyr Ala Ile Asp Gln Ala Ala Asn Leu Val
            660                 665                 670

Glu Cys Leu Ser Asp Glu Phe Cys Asp Gln Glu Lys Met Ile Leu Leu
        675                 680                 685

Asp Gln Val Lys Phe Ala Lys Arg Leu Ser Gln Ala Arg Asn Leu Leu
```

-continued

```
            690                 695                 700
Asn Tyr Gly Asp Phe Glu Ser Pro Asp Trp Ser Gly Glu Asn Gly Trp
705                     710                 715                 720

Lys Thr Ser Pro His Val His Val Ala Ser Asp Asn Pro Ile Phe Lys
                    725                 730                 735

Gly Arg Tyr Leu His Met Pro Gly Ala Asn Gln Pro Gln Met Ser Asp
                    740                 745                 750

Thr Val Tyr Pro Thr Tyr Leu Tyr Gln Lys Val Asp Glu Ser Lys Leu
                755                 760                 765

Lys Ser Tyr Thr Arg Tyr His Val Arg Gly Phe Val Gly Asn Ser Lys
            770                 775                 780

Asp Leu Ala Leu Leu Val Glu Arg Tyr Gly Lys Glu Val His Val Glu
785                 790                 795                 800

Met Asp Val Pro Asn Asp Ile Arg Tyr Thr Leu Pro Met Asn Glu Cys
                805                 810                 815

Gly Gly Phe Asp Arg Cys Gly His Ser Ser Tyr Gln Ala Gly Thr Asp
                820                 825                 830

Ser His Thr Cys Thr Cys Lys Asp Pro Ala Gln Met Asp Ala Ala Cys
            835                 840                 845

Gln Cys Lys Asp Lys Ser Lys Arg Thr Ala Ser Gly Val Tyr Thr Asn
        850                 855                 860

Val Tyr Ala Gly Ser Asp Met Met Tyr Leu Asp Gly Tyr His Ala His
865                 870                 875                 880

Thr Ser Cys Gly Cys Lys Asp Pro His Val Phe Ser Phe His Ile Asp
                885                 890                 895

Thr Gly Cys Val Asp Val Glu Glu Asn Ala Gly Leu Leu Phe Ala Leu
            900                 905                 910

Lys Ile Ala Ser Thr Asp Gly Val Ala Asn Ile Asp Asn Leu Glu Ile
            915                 920                 925

Ile Glu Gly Gln Pro Leu Thr Gly Glu Ala Leu Ala Arg Val Lys Lys
        930                 935                 940

Arg Glu His Lys Trp Lys Glu Arg Lys Gln Lys Arg Cys Lys Thr
945                 950                 955                 960

Lys Glu Ala Val Glu Ala Thr Leu Thr Ala Ile Asn Ala Leu Phe Thr
                965                 970                 975

Asn Lys Gln Tyr Asn Arg Leu Lys Phe Glu Thr Leu Phe Pro His Ile
            980                 985                 990

Leu His Ala Asp Glu Leu Val Lys Arg Ile Pro Tyr Val Tyr His Pro
        995                 1000                1005

Phe Leu Arg Gly Ala Tyr Pro Glu Val Pro Gly Met Asn Tyr Asp
1010                1015                1020

Ile Phe Gln Gln Leu Ser Ala Leu Val Ala Arg Ala Arg Gly Leu
    1025                1030                1035

Tyr Asp Met Arg Asn Leu Val Gln Asn Gly Thr Phe Ser Ala Gly
    1040                1045                1050

Ile Gly Asn Trp Gln Val Thr Asp Gly Val Thr Thr Arg Leu Glu
    1055                1060                1065

Gly Asn Thr Ser Val Leu Val Leu Arg Glu Trp Ser Asp Lys Ala
    1070                1075                1080

Leu Gln His Leu Arg Ile Asp Ala Glu Arg Gly Tyr Val Leu Arg
    1085                1090                1095

Val Thr Ala Arg Lys Glu Gly Asn Gly Asp Gly Tyr Val Val Ile
    1100                1105                1110
```

His Asp Cys Asp Asn Gln Gln Glu Lys Val Thr Phe Thr Ala Cys
1115 1120 1125

Asp Ser Ser Thr Met Gly Ala Ser Thr Gly Thr Gln Ala Thr Val
1130 1135 1140

Ile Pro Ala Thr Asn Cys Pro Pro Cys His Ser Gly Thr Trp Gly
1145 1150 1155

Glu Glu Met Thr Leu Pro Val Thr Met Leu Ser Gly Tyr Val Thr
1160 1165 1170

Lys Thr Ala Glu Ile Phe Pro Asp Thr Asp Arg Ile Arg Val Glu
1175 1180 1185

Ile Gly Glu Thr Glu Gly Thr Phe Lys Val Glu Ser Val Glu Leu
1190 1195 1200

Ile Cys Met Glu His Met Glu Asp His Met Tyr Asp Met Ala Gly
1205 1210 1215

Asn Leu Glu Glu Glu Met Gln Gly Leu Gly Ile Glu Ser Ser His
1220 1225 1230

Ala Val Thr Tyr Glu Met Cys Phe Ser Trp Asp Ile Gln Cys Pro
1235 1240 1245

Met Glu Ala Ser Ile Pro Pro Ile Val Pro Pro Thr Thr Met Tyr
1250 1255 1260

Asp Met Ala Gly Asn Val Glu Glu Glu Ile Arg Tyr Leu
1265 1270 1275

<210> SEQ ID NO 7
<211> LENGTH: 627
<212> TYPE: PRT
<213> ORGANISM: Bacillus thuringiensis

<400> SEQUENCE: 7

Met Lys Gln Asn Ser Asn Asp Glu Tyr Glu Ile Leu Asp Ser Lys Gly
1 5 10 15

Met His Asp Pro Tyr Lys Lys Phe Pro Ile His His Thr Ser Ser Pro
20 25 30

Ser Phe Asp Phe Lys Met Gly Arg Gln Lys Glu Ile Asp Thr Leu Ser
35 40 45

Leu Ile Pro Glu Glu Ile Ser Pro Leu Phe Asn Pro Ala Ala Ile Ile
50 55 60

Thr Ala Ala Lys Val Leu Phe Asn Ile Gly Ser Lys Ile Ala Ser Gly
65 70 75 80

Lys Arg Phe Leu Asp Ser Val Leu Ala Ile Leu Trp Pro Glu Ala Ala
85 90 95

Ala Gln Ser Lys Trp Glu Glu Phe Ile Ala Leu Ala Glu Gln Leu Ile
100 105 110

Gln Glu Lys Ile Ala Glu Tyr Ala Arg Gly Ala Ala Ile Ala Lys Leu
115 120 125

Ile Gly Leu Lys Asp Val Met Met Val Tyr Glu Gly Ala Phe Ala Asp
130 135 140

Trp Glu Lys Asn Gln Thr Asp Pro Gln Lys Gln Glu Ala Val Arg Asn
145 150 155 160

Glu Phe Arg Asn Ala Asn Asp Ile Ile Val Ala Ala Met Pro Glu Phe
165 170 175

Ala Ile Lys Asn Tyr Glu Ile Gln Leu Leu Thr Val Tyr Ala Glu Ala
180 185 190

Ala Asn Leu His Leu Thr Leu Leu Arg Asp Ala Ser Ile Tyr Gly Leu

```
            195                 200                 205
Gln Trp Gly Met Gly Gln Ser Glu Val Asp Arg His Tyr Thr Ala Gln
210                 215                 220

Met Ser Arg Thr Gln Thr Tyr Thr Asp Tyr Cys Val Ser Trp Tyr Asp
225                 230                 235                 240

Ile Gly Leu Glu Lys Ala Lys Lys Leu Lys Ala Asn Ile Tyr Asp Arg
                245                 250                 255

Asp Gln Tyr Pro Trp Ile Gly Ala Gly Pro Pro Pro Gly Tyr Pro Met
            260                 265                 270

Ser Ile Phe Gln Thr Thr Glu Asp Trp Asn Leu Phe Asn Asn Phe Arg
        275                 280                 285

Arg Asp Met Thr Leu Gln Val Leu Asp Leu Val Ala Tyr Trp Pro Thr
    290                 295                 300

Tyr Asp Val Lys Lys Tyr Pro Ile Ser Thr Gln Val Gln Leu Thr Arg
305                 310                 315                 320

Asp Ile Tyr Thr Asn Ile Trp Gly Ile Asp Asn Thr Ser Val Asp Lys
                325                 330                 335

Ile Glu Ala Gln Phe Val Arg Pro Pro His Leu Val Thr His Leu Asp
            340                 345                 350

Ala Leu Asp Phe Tyr Val Asp Tyr Asn Leu His Phe Asn Gly Ser Glu
        355                 360                 365

Asn Ile Met Gly Glu Arg Lys Val Tyr Asn Tyr Thr Ser Glu Arg Glu
    370                 375                 380

Ile Glu Ser Pro Ile Ser Gly Lys Gln Thr Gln Asn Lys Lys Thr Leu
385                 390                 395                 400

Thr Val Arg Gly Asn Pro Ala Asn Thr Ile Arg Cys Trp His Tyr Val
                405                 410                 415

Glu Ala Ser Ile Leu Asp Phe Pro Gly Arg Leu Arg Ile Gly Asn Val
            420                 425                 430

Val Ser Gly Trp Gly Gly Ala Trp Ser Thr Ala Glu Ile Pro Asp Asn
        435                 440                 445

His Ile Ser Trp Ile Thr Thr Thr Phe Pro Thr Pro Ser Leu Val Ile
    450                 455                 460

Lys Gly Met Arg Ala Val Gly Phe Ser Trp Met Ser Asn Thr Val Asp
465                 470                 475                 480

Pro Thr Asn Thr Val Ala Pro Gly Arg Ile Thr Gln Ile Pro Ala Val
                485                 490                 495

Lys Ala Arg Asp Ile Gly Pro Gly Gly Arg Val Ile Lys Gly Pro Gly
            500                 505                 510

Thr Thr Gly Gly Asp Leu Val Glu Leu Asn Ala Ala Leu Thr Thr Gly
        515                 520                 525

Ile Ser Leu Asn Ile Ser Ser Pro Gln Asn Glu Val Tyr Thr Met Arg
    530                 535                 540

Ile Arg Tyr Ala Ser Arg Gly Asn Gly Gln Leu Arg Leu Thr Thr Tyr
545                 550                 555                 560

Gln Tyr Ser Gly Tyr Ala Pro Arg Ile Val Asn Phe Asn Ala Thr Asp
                565                 570                 575

Ser Ser Gly Ser Leu Lys Phe Asn Ser Phe Asn Tyr Leu Thr Ile Gly
            580                 585                 590

Asn Val Ala Ala Asp Pro Thr Ala Leu Pro Arg Phe Val Phe Asp Leu
        595                 600                 605

Tyr Ser Gly Ser Pro Ile Ile Ile Asp Lys Ile Glu Phe Leu Pro Arg
    610                 615                 620
```

Gly Ile Ile
625

<210> SEQ ID NO 8
<211> LENGTH: 1260
<212> TYPE: PRT
<213> ORGANISM: Bacillus thuringiensis

<400

```
                355                 360                 365
Ile Glu Ser Pro Ile Ser Gly Lys Gln Thr Gln Asn Lys Lys Thr Leu
370                 375                 380

Thr Val Arg Gly Asn Pro Ala Asn Thr Ile Arg Cys Trp His Tyr Val
385                 390                 395                 400

Glu Ala Ser Ile Leu Asp Phe Pro Gly Arg Leu Arg Ile Gly Asn Val
                405                 410                 415

Val Ser Gly Trp Gly Ala Trp Ser Thr Ala Glu Ile Pro Asp Asn
                420                 425                 430

His Ile Ser Trp Ile Thr Thr Thr Phe Pro Thr Pro Ser Leu Val Ile
                435                 440                 445

Lys Gly Met Arg Ala Val Gly Phe Ser Trp Met Ser Asn Thr Val Asp
                450                 455                 460

Pro Thr Asn Thr Val Ala Pro Gly Arg Ile Thr Gln Ile Pro Ala Val
465                 470                 475                 480

Lys Ala Arg Asp Ile Gly Pro Gly Gly Arg Val Ile Lys Gly Pro Gly
                485                 490                 495

Thr Thr Gly Gly Asp Leu Val Glu Leu Asn Ala Ala Leu Thr Thr Gly
                500                 505                 510

Ile Ser Leu Asn Ile Ser Ser Pro Gln Asn Glu Val Tyr Thr Met Arg
                515                 520                 525

Ile Arg Tyr Ala Ser Arg Gly Asn Gly Gln Leu Arg Leu Thr Thr Tyr
                530                 535                 540

Gln Tyr Ser Gly Tyr Ala Pro Arg Ile Val Asn Phe Asn Ala Thr Asp
545                 550                 555                 560

Ser Ser Gly Ser Leu Lys Phe Asn Ser Phe Asn Tyr Leu Thr Ile Gly
                565                 570                 575

Asn Val Ala Ala Asp Pro Thr Ala Leu Pro Arg Phe Val Phe Asp Leu
                580                 585                 590

Tyr Ser Gly Ser Pro Ile Ile Ile Asp Lys Ile Glu Phe Leu Pro Arg
                595                 600                 605

Gly Ile Ile Leu Glu Glu Ala Glu Ala Asn Gln Asp Leu Glu Lys Ala
                610                 615                 620

Arg Lys Ala Val Asn Ala Leu Phe Thr Asn Asp Ala Lys Asp Asn Leu
625                 630                 635                 640

Lys Leu Asn Met Thr Asp Tyr Ala Ile Asp Gln Ala Ala Asn Leu Val
                645                 650                 655

Glu Cys Leu Ser Asp Glu Phe Cys Asp Gln Glu Lys Met Ile Leu Leu
                660                 665                 670

Asp Gln Val Lys Phe Ala Lys Arg Leu Ser Gln Ala Arg Asn Leu Leu
                675                 680                 685

Asn Tyr Gly Asp Phe Glu Ser Pro Asp Trp Ser Gly Glu Asn Gly Trp
                690                 695                 700

Lys Thr Ser Pro His Val His Val Ala Ser Asp Asn Pro Ile Phe Lys
705                 710                 715                 720

Gly Arg Tyr Leu His Met Pro Gly Ala Asn Gln Pro Gln Met Ser Asp
                725                 730                 735

Thr Val Tyr Pro Thr Tyr Leu Tyr Gln Lys Val Asp Glu Ser Lys Leu
                740                 745                 750

Lys Ser Tyr Thr Arg Tyr His Val Arg Gly Phe Val Gly Asn Ser Lys
                755                 760                 765

Asp Leu Ala Leu Leu Val Glu Arg Tyr Gly Lys Glu Val His Val Glu
                770                 775                 780
```

```
Met Asp Val Pro Asn Asp Ile Arg Tyr Thr Leu Pro Met Asn Glu Cys
785                 790                 795                 800

Gly Gly Phe Asp Arg Cys Gly His Ser Ser Tyr Gln Ala Gly Thr Asp
        805                 810                 815

Ser His Thr Cys Thr Cys Lys Asp Pro Ala Gln Met Ala Ala Cys
            820                 825                 830

Gln Cys Lys Asp Lys Ser Lys Arg Thr Ala Ser Gly Val Tyr Thr Asn
        835                 840                 845

Val Tyr Ala Gly Ser Asp Met Met Tyr Leu Asp Gly Tyr His Ala His
850                 855                 860

Thr Ser Cys Gly Cys Lys Asp Pro His Val Phe Ser Phe His Ile Asp
865                 870                 875                 880

Thr Gly Cys Val Asp Val Glu Glu Asn Ala Gly Leu Leu Phe Ala Leu
            885                 890                 895

Lys Ile Ala Ser Thr Asp Gly Val Ala Asn Ile Asp Asn Leu Glu Ile
            900                 905                 910

Ile Glu Gly Gln Pro Leu Thr Gly Glu Ala Leu Ala Arg Val Lys Lys
        915                 920                 925

Arg Glu His Lys Trp Lys Glu Arg Lys Gln Lys Arg Cys Lys Thr
930                 935                 940

Lys Glu Ala Val Glu Ala Thr Leu Thr Ala Ile Asn Ala Leu Phe Thr
945                 950                 955                 960

Asn Lys Gln Tyr Asn Arg Leu Lys Phe Glu Thr Leu Phe Pro His Ile
            965                 970                 975

Leu His Ala Asp Glu Leu Val Lys Arg Ile Pro Tyr Val Tyr His Pro
            980                 985                 990

Phe Leu Arg Gly Ala Tyr Pro Glu  Val Pro Gly Met Asn  Tyr Asp Ile
        995                 1000                1005

Phe Gln  Gln Leu Ser Ala Leu  Val Ala Arg Ala Arg  Gly Leu Tyr
    1010                1015                1020

Asp Met  Arg Asn Leu Val Gln  Asn Gly Thr Phe Ser  Ala Gly Ile
    1025                1030                1035

Gly Asn  Trp Gln Val Thr Asp  Gly Val Thr Thr Arg  Leu Glu Gly
    1040                1045                1050

Asn Thr  Ser Val Leu Val Leu  Arg Glu Trp Ser Asp  Lys Ala Leu
    1055                1060                1065

Gln His  Leu Arg Ile Asp Ala  Glu Arg Gly Tyr Val  Leu Arg Val
    1070                1075                1080

Thr Ala  Arg Lys Glu Gly Asn  Gly Asp Gly Tyr Val  Val Ile His
    1085                1090                1095

Asp Cys  Asp Asn Gln Gln Glu  Lys Val Thr Phe Thr  Ala Cys Asp
    1100                1105                1110

Ser Ser  Thr Met Gly Ala Ser  Thr Gly Thr Gln Ala  Thr Val Ile
    1115                1120                1125

Pro Ala  Thr Asn Cys Pro Pro  Cys His Ser Gly Thr  Trp Gly Glu
    1130                1135                1140

Glu Met  Thr Leu Pro Val Thr  Met Leu Ser Gly Tyr  Val Thr Lys
    1145                1150                1155

Thr Ala  Glu Ile Phe Pro Asp  Thr Asp Arg Ile Arg  Val Glu Ile
    1160                1165                1170

Gly Glu  Thr Glu Gly Thr Phe  Lys Val Glu Ser Val  Glu Leu Ile
    1175                1180                1185
```

```
Cys Met Glu His Met Glu Asp His Met Tyr Asp Met Ala Gly Asn
    1190                1195                1200

Leu Glu Glu Met Gln Gly Leu Gly Ile Glu Ser Ser His Ala
    1205                1210                1215

Val Thr Tyr Glu Met Cys Phe Ser Trp Asp Ile Gln Cys Pro Met
    1220                1225                1230

Glu Ala Ser Ile Pro Pro Ile Val Pro Pro Thr Thr Met Tyr Asp
    1235                1240                1245

Met Ala Gly Asn Val Glu Glu Glu Ile Arg Tyr Leu
    1250                1255                1260

<210> SEQ ID NO 9
<211> LENGTH: 1239
<212> TYPE: PRT
<213> ORGANISM: Bacillus thuringiensis

<400> SEQUENCE: 9

Met Gly Arg Gln Lys Glu Ile Asp Thr Leu Ser Leu Ile Pro Glu Glu
1               5                   10                  15

Ile Ser Pro Leu Phe Asn Pro Ala Ala Ile Thr Ala Ala Lys Val
                20                  25                  30

Leu Phe Asn Ile Gly Ser Lys Ile Ala Ser Gly Lys Arg Phe Leu Asp
            35                  40                  45

Ser Val Leu Ala Ile Leu Trp Pro Glu Ala Ala Gln Ser Lys Trp
    50                  55                  60

Glu Glu Phe Ile Ala Leu Ala Glu Gln Leu Ile Gln Glu Lys Ile Ala
65                  70                  75                  80

Glu Tyr Ala Arg Gly Ala Ala Ile Ala Lys Leu Ile Gly Leu Lys Asp
                85                  90                  95

Val Met Met Val Tyr Glu Gly Ala Phe Ala Asp Trp Glu Lys Asn Gln
                100                 105                 110

Thr Asp Pro Gln Lys Gln Glu Ala Val Arg Asn Glu Phe Arg Asn Ala
            115                 120                 125

Asn Asp Ile Ile Val Ala Ala Met Pro Glu Phe Ala Ile Lys Asn Tyr
130                 135                 140

Glu Ile Gln Leu Leu Thr Val Tyr Ala Glu Ala Ala Asn Leu His Leu
145                 150                 155                 160

Thr Leu Leu Arg Asp Ala Ser Ile Tyr Gly Leu Gln Trp Gly Met Gly
                165                 170                 175

Gln Ser Glu Val Asp Arg His Tyr Thr Ala Gln Met Ser Arg Thr Gln
            180                 185                 190

Thr Tyr Thr Asp Tyr Cys Val Ser Trp Tyr Asp Ile Gly Leu Glu Lys
        195                 200                 205

Ala Lys Lys Leu Lys Ala Asn Ile Tyr Asp Arg Asp Gln Tyr Pro Trp
    210                 215                 220

Ile Gly Ala Gly Pro Pro Gly Tyr Pro Met Ser Ile Phe Gln Thr
225                 230                 235                 240

Thr Glu Asp Trp Asn Leu Phe Asn Asn Phe Arg Arg Asp Met Thr Leu
                245                 250                 255

Gln Val Leu Asp Leu Val Ala Tyr Trp Pro Thr Tyr Asp Val Lys Lys
            260                 265                 270

Tyr Pro Ile Ser Thr Gln Val Gln Leu Thr Arg Asp Ile Tyr Thr Asn
        275                 280                 285

Ile Trp Gly Ile Asp Asn Thr Ser Val Asp Lys Ile Glu Ala Gln Phe
    290                 295                 300
```

-continued

```
Val Arg Pro Pro His Leu Val Thr His Leu Asp Ala Leu Asp Phe Tyr
305                 310                 315                 320

Val Asp Tyr Asn Leu His Phe Asn Gly Ser Glu Asn Ile Met Gly Glu
            325                 330                 335

Arg Lys Val Tyr Asn Tyr Thr Ser Glu Arg Glu Ile Glu Ser Pro Ile
        340                 345                 350

Ser Gly Lys Gln Thr Gln Asn Lys Lys Thr Leu Thr Val Arg Gly Asn
    355                 360                 365

Pro Ala Asn Thr Ile Arg Cys Trp His Tyr Val Glu Ala Ser Ile Leu
370                 375                 380

Asp Phe Pro Gly Arg Leu Arg Ile Gly Asn Val Val Ser Gly Trp Gly
385                 390                 395                 400

Gly Ala Trp Ser Thr Ala Glu Ile Pro Asp Asn His Ile Ser Trp Ile
            405                 410                 415

Thr Thr Thr Phe Pro Thr Pro Ser Leu Val Ile Lys Gly Met Arg Ala
            420                 425                 430

Val Gly Phe Ser Trp Met Ser Asn Thr Val Asp Pro Thr Asn Thr Val
        435                 440                 445

Ala Pro Gly Arg Ile Thr Gln Ile Pro Ala Val Lys Ala Arg Asp Ile
450                 455                 460

Gly Pro Gly Gly Arg Val Ile Lys Gly Pro Gly Thr Thr Gly Gly Asp
465                 470                 475                 480

Leu Val Glu Leu Asn Ala Ala Leu Thr Thr Gly Ile Ser Leu Asn Ile
            485                 490                 495

Ser Ser Pro Gln Asn Glu Val Tyr Thr Met Arg Ile Arg Tyr Ala Ser
            500                 505                 510

Arg Gly Asn Gly Gln Leu Arg Leu Thr Thr Tyr Gln Tyr Ser Gly Tyr
        515                 520                 525

Ala Pro Arg Ile Val Asn Phe Asn Ala Thr Asp Ser Ser Gly Ser Leu
530                 535                 540

Lys Phe Asn Ser Phe Asn Tyr Leu Thr Ile Gly Asn Val Ala Ala Asp
545                 550                 555                 560

Pro Thr Ala Leu Pro Arg Phe Val Phe Asp Leu Tyr Ser Gly Ser Pro
            565                 570                 575

Ile Ile Ile Asp Lys Ile Glu Phe Leu Pro Arg Gly Ile Ile Leu Glu
            580                 585                 590

Glu Ala Glu Ala Asn Gln Asp Leu Glu Lys Ala Arg Lys Ala Val Asn
        595                 600                 605

Ala Leu Phe Thr Asn Asp Ala Lys Asp Asn Leu Lys Leu Asn Met Thr
610                 615                 620

Asp Tyr Ala Ile Asp Gln Ala Ala Asn Leu Val Glu Cys Leu Ser Asp
625                 630                 635                 640

Glu Phe Cys Asp Gln Glu Lys Met Ile Leu Leu Asp Gln Val Lys Phe
            645                 650                 655

Ala Lys Arg Leu Ser Gln Ala Arg Asn Leu Leu Asn Tyr Gly Asp Phe
        660                 665                 670

Glu Ser Pro Asp Trp Ser Gly Glu Asn Gly Trp Lys Thr Ser Pro His
            675                 680                 685

Val His Val Ala Ser Asp Asn Pro Ile Phe Lys Gly Arg Tyr Leu His
        690                 695                 700

Met Pro Gly Ala Asn Gln Pro Gln Met Ser Asp Thr Val Tyr Pro Thr
705                 710                 715                 720
```

-continued

```
Tyr Leu Tyr Gln Lys Val Asp Glu Ser Lys Leu Lys Ser Tyr Thr Arg
            725                 730                 735

Tyr His Val Arg Gly Phe Val Gly Asn Ser Lys Asp Leu Ala Leu Leu
            740                 745                 750

Val Glu Arg Tyr Gly Lys Glu Val His Val Glu Met Asp Val Pro Asn
            755                 760                 765

Asp Ile Arg Tyr Thr Leu Pro Met Asn Glu Cys Gly Gly Phe Asp Arg
            770                 775                 780

Cys Gly His Ser Ser Tyr Gln Ala Gly Thr Asp Ser His Thr Cys Thr
785                 790                 795                 800

Cys Lys Asp Pro Ala Gln Met Asp Ala Ala Cys Gln Cys Lys Asp Lys
            805                 810                 815

Ser Lys Arg Thr Ala Ser Gly Val Tyr Thr Asn Val Tyr Ala Gly Ser
            820                 825                 830

Asp Met Met Tyr Leu Asp Gly Tyr His Ala His Thr Ser Cys Gly Cys
            835                 840                 845

Lys Asp Pro His Val Phe Ser Phe His Ile Asp Thr Gly Cys Val Asp
            850                 855                 860

Val Glu Glu Asn Ala Gly Leu Leu Phe Ala Leu Lys Ile Ala Ser Thr
865                 870                 875                 880

Asp Gly Val Ala Asn Ile Asp Asn Leu Glu Ile Ile Glu Gly Gln Pro
            885                 890                 895

Leu Thr Gly Glu Ala Leu Ala Arg Val Lys Lys Arg Glu His Lys Trp
            900                 905                 910

Lys Glu Glu Arg Lys Gln Lys Arg Cys Lys Thr Lys Gly Ala Val Glu
            915                 920                 925

Ala Thr Leu Thr Ala Ile Asn Ala Leu Phe Thr Asn Lys Gln Tyr Asn
            930                 935                 940

Arg Leu Lys Phe Glu Thr Leu Phe Pro His Ile Leu His Ala Asp Glu
945                 950                 955                 960

Leu Val Lys Arg Ile Pro Tyr Val Tyr His Pro Phe Leu Arg Gly Ala
            965                 970                 975

Tyr Pro Glu Val Pro Gly Met Asn Tyr Asp Ile Phe Gln Gln Leu Ser
            980                 985                 990

Ala Leu Val Ala Arg Ala Arg Gly Leu Tyr Asp Met Arg Asn Leu Val
            995                1000                1005

Gln Asn Gly Thr Phe Ser Ala Gly Ile Gly Asn Trp Gln Val Thr
           1010                1015                1020

Asp Gly Val Thr Thr Arg Leu Glu Gly Asn Thr Ser Val Leu Val
           1025                1030                1035

Leu Arg Glu Trp Ser Asp Lys Ala Leu Gln His Leu Arg Ile Asp
           1040                1045                1050

Ala Glu Arg Gly Tyr Val Leu Arg Val Thr Ala Arg Lys Glu Gly
           1055                1060                1065

Asn Gly Asp Gly Tyr Val Val Ile His Asp Cys Asp Asn Gln Gln
           1070                1075                1080

Glu Lys Val Thr Phe Thr Ala Cys Asp Ser Ser Thr Met Gly Ala
           1085                1090                1095

Ser Thr Gly Thr Gln Ala Thr Val Ile Pro Ala Thr Asn Cys Pro
           1100                1105                1110

Pro Cys His Ser Gly Thr Trp Gly Glu Glu Met Thr Leu Pro Val
           1115                1120                1125

Thr Met Leu Ser Gly Tyr Val Thr Lys Thr Ala Glu Ile Phe Pro
```

```
                1130               1135                1140
Asp Thr  Asp Arg Ile Arg Val Glu Ile Gly Glu Thr Glu Gly Thr
        1145                1150                1155

Phe Lys  Val Glu Ser Val Glu Leu Ile Cys Met Glu His Met Glu
        1160                1165                1170

Asp His  Met Tyr Asp Met Ala Gly Asn Leu Glu Glu Glu Met Gln
        1175                1180                1185

Gly Leu  Gly Ile Glu Ser Ser His Ala Val Thr Tyr Glu Met Cys
        1190                1195                1200

Phe Ser  Trp Asp Ile Gln Cys Pro Met Glu Ala Ser Ile Pro Pro
        1205                1210                1215

Ile Val  Pro Pro Thr Thr Met Tyr Asp Met Ala Gly Asn Val Glu
        1220                1225                1230

Glu Glu  Ile Arg Tyr Leu
        1235

<210> SEQ ID NO 10
<211> LENGTH: 611
<212> TYPE: PRT
<213> ORGANISM: Bacillus thuringiensis

<400> SEQUENCE: 10

Met His Asp Pro Tyr Lys Lys Phe Pro Ile His His Thr Ser Pro
1               5                  10                  15

Ser Phe Asp Phe Lys Met Gly Arg Gln Lys Glu Ile Asp Thr Leu Ser
                20                  25                  30

Leu Ile Pro Glu Glu Ile Ser Pro Leu Phe Asn Pro Ala Ala Ile Ile
            35                  40                  45

Thr Ala Ala Lys Val Leu Phe Asn Ile Gly Ser Lys Ile Ala Ser Gly
        50                  55                  60

Lys Arg Phe Leu Asp Ser Val Leu Ala Ile Leu Trp Pro Glu Ala Ala
65                  70                  75                  80

Ala Gln Ser Lys Trp Glu Glu Phe Ile Ala Leu Ala Glu Gln Leu Ile
                85                  90                  95

Gln Glu Lys Ile Ala Glu Tyr Ala Arg Gly Ala Ala Ile Ala Lys Leu
            100                 105                 110

Ile Gly Leu Lys Asp Val Met Met Val Tyr Glu Gly Ala Phe Ala Asp
        115                 120                 125

Trp Glu Lys Asn Gln Thr Asp Pro Gln Lys Gly Glu Ala Val Arg Asn
130                 135                 140

Glu Phe Arg Asn Ala Asn Asp Ile Ile Val Ala Ala Met Pro Glu Phe
145                 150                 155                 160

Ala Ile Lys Asn Tyr Glu Ile Gln Leu Leu Thr Val Tyr Ala Glu Ala
                165                 170                 175

Ala Asn Leu His Leu Thr Leu Leu Arg Asp Ala Ser Ile Tyr Gly Leu
            180                 185                 190

Gln Trp Gly Met Gly Gln Ser Glu Val Asp Arg His Tyr Thr Ala Gln
        195                 200                 205

Met Ser Arg Thr Gln Thr Tyr Thr Asp Tyr Cys Val Ser Trp Tyr Asp
    210                 215                 220

Ile Gly Leu Glu Lys Ala Lys Lys Leu Lys Ala Asn Ile Tyr Asp Arg
225                 230                 235                 240

Asp Gln Tyr Pro Trp Ile Gly Ala Gly Pro Pro Pro Gly Tyr Pro Met
                245                 250                 255
```

```
Ser Ile Phe Gln Thr Thr Glu Asp Trp Asn Leu Phe Asn Asn Phe Arg
            260                 265                 270

Arg Asp Met Thr Leu Gln Val Leu Asp Leu Val Ala Tyr Trp Pro Thr
        275                 280                 285

Tyr Asp Val Lys Lys Tyr Pro Ile Ser Thr Gln Val Gln Leu Thr Arg
    290                 295                 300

Asp Ile Tyr Thr Asn Ile Trp Gly Ile Asp Asn Thr Ser Val Asp Lys
305                 310                 315                 320

Ile Glu Ala Gln Phe Val Arg Pro Pro His Leu Val Thr His Leu Asp
                325                 330                 335

Ala Leu Asp Phe Tyr Val Asp Tyr Asn Leu His Phe Asn Gly Ser Glu
            340                 345                 350

Asn Ile Met Gly Glu Arg Lys Val Tyr Asn Tyr Thr Ser Glu Arg Glu
        355                 360                 365

Ile Glu Ser Pro Ile Ser Gly Lys Gln Thr Gln Asn Lys Lys Thr Leu
    370                 375                 380

Thr Val Arg Gly Asn Pro Ala Asn Thr Ile Arg Cys Trp His Tyr Val
385                 390                 395                 400

Glu Ala Ser Ile Leu Asp Phe Pro Gly Arg Leu Arg Ile Gly Asn Val
                405                 410                 415

Val Ser Gly Trp Gly Ala Trp Ser Thr Ala Glu Ile Pro Asp Asn
            420                 425                 430

His Ile Ser Trp Ile Thr Thr Thr Phe Pro Thr Pro Ser Leu Val Ile
        435                 440                 445

Lys Gly Met Arg Ala Val Gly Phe Ser Trp Met Ser Asn Thr Val Asp
450                 455                 460

Pro Thr Asn Thr Val Ala Pro Gly Arg Ile Thr Gln Ile Pro Ala Val
465                 470                 475                 480

Lys Ala Arg Asp Ile Gly Pro Gly Gly Arg Val Ile Lys Gly Pro Gly
                485                 490                 495

Thr Thr Gly Gly Asp Leu Val Glu Leu Asn Ala Ala Leu Thr Thr Gly
            500                 505                 510

Ile Ser Leu Asn Ile Ser Ser Pro Gln Asn Glu Val Tyr Thr Met Arg
        515                 520                 525

Ile Arg Tyr Ala Ser Arg Gly Asn Gly Gln Leu Arg Leu Thr Thr Tyr
    530                 535                 540

Gln Tyr Ser Gly Tyr Ala Pro Arg Ile Val Asn Phe Asn Ala Thr Asp
545                 550                 555                 560

Ser Ser Gly Ser Leu Lys Phe Asn Ser Phe Asn Tyr Leu Thr Ile Gly
                565                 570                 575

Asn Val Ala Ala Asp Pro Thr Ala Leu Pro Arg Phe Val Phe Asp Leu
            580                 585                 590

Tyr Ser Gly Ser Pro Ile Ile Ile Asp Lys Ile Glu Phe Leu Pro Arg
        595                 600                 605

Gly Ile Ile
    610

<210> SEQ ID NO 11
<211> LENGTH: 590
<212> TYPE: PRT
<213> ORGANISM: Bacillus thuringiensis

<400> SEQUENCE: 11

Met Gly Arg Gln Lys Glu Ile Asp Thr Leu Ser Leu Ile Pro Glu Glu
1               5                   10                  15
```

-continued

Ile Ser Pro Leu Phe Asn Pro Ala Ala Ile Thr Ala Ala Lys Val
         20                  25                  30

Leu Phe Asn Ile Gly Ser Lys Ile Ala Ser Gly Lys Arg Phe Leu Asp
         35                  40                  45

Ser Val Leu Ala Ile Leu Trp Pro Glu Ala Ala Gln Ser Lys Trp
 50                  55                  60

Glu Glu Phe Ile Ala Leu Ala Glu Gln Leu Ile Gln Glu Lys Ile Ala
 65                  70                  75                  80

Glu Tyr Ala Arg Gly Ala Ala Ile Ala Lys Leu Ile Gly Leu Lys Asp
                 85                  90                  95

Val Met Met Val Tyr Glu Gly Ala Phe Ala Asp Trp Glu Lys Asn Gln
                 100                 105                 110

Thr Asp Pro Gln Lys Gln Glu Ala Val Arg Asn Glu Phe Arg Asn Ala
                 115                 120                 125

Asn Asp Ile Ile Val Ala Ala Met Pro Glu Phe Ala Ile Lys Asn Tyr
         130                 135                 140

Glu Ile Gln Leu Leu Thr Val Tyr Ala Glu Ala Ala Asn Leu His Leu
145                 150                 155                 160

Thr Leu Leu Arg Asp Ala Ser Ile Tyr Gly Leu Gln Trp Gly Met Gly
                 165                 170                 175

Gln Ser Glu Val Asp Arg His Tyr Thr Ala Gln Met Ser Arg Thr Gln
                 180                 185                 190

Thr Tyr Thr Asp Tyr Cys Val Ser Trp Tyr Asp Ile Gly Leu Glu Lys
         195                 200                 205

Ala Lys Lys Leu Lys Ala Asn Ile Tyr Asp Arg Asp Gln Tyr Pro Trp
         210                 215                 220

Ile Gly Ala Gly Pro Pro Gly Tyr Pro Met Ser Ile Phe Gln Thr
225                 230                 235                 240

Thr Glu Asp Trp Asn Leu Phe Asn Asn Phe Arg Arg Asp Met Thr Leu
                 245                 250                 255

Gln Val Leu Asp Leu Val Ala Tyr Trp Pro Thr Tyr Asp Val Lys Lys
                 260                 265                 270

Tyr Pro Ile Ser Thr Gln Val Gln Leu Thr Arg Asp Ile Tyr Thr Asn
         275                 280                 285

Ile Trp Gly Ile Asp Asn Thr Ser Val Asp Lys Ile Glu Ala Gln Phe
290                 295                 300

Val Arg Pro Pro His Leu Val Thr His Leu Asp Ala Leu Asp Phe Tyr
305                 310                 315                 320

Val Asp Tyr Asn Leu His Phe Asn Gly Ser Glu Asn Ile Met Gly Glu
                 325                 330                 335

Arg Lys Val Tyr Asn Tyr Thr Ser Glu Arg Glu Ile Glu Ser Pro Ile
                 340                 345                 350

Ser Gly Lys Gln Thr Gln Asn Lys Lys Thr Leu Thr Val Arg Gly Asn
         355                 360                 365

Pro Ala Asn Thr Ile Arg Cys Trp His Tyr Val Glu Ala Ser Ile Leu
         370                 375                 380

Asp Phe Pro Gly Arg Leu Arg Ile Gly Asn Val Val Ser Gly Trp Gly
385                 390                 395                 400

Gly Ala Trp Ser Thr Ala Glu Ile Pro Asp Asn His Ile Ser Trp Ile
                 405                 410                 415

Thr Thr Thr Phe Pro Thr Pro Ser Leu Val Ile Lys Gly Met Arg Ala
                 420                 425                 430

```
Val Gly Phe Ser Trp Met Ser Asn Thr Val Asp Pro Thr Asn Thr Val
            435                 440                 445

Ala Pro Gly Arg Ile Thr Gln Ile Pro Ala Val Lys Ala Arg Asp Ile
450                 455                 460

Gly Pro Gly Gly Arg Val Ile Lys Gly Pro Gly Thr Thr Gly Gly Asp
465                 470                 475                 480

Leu Val Glu Leu Asn Ala Ala Leu Thr Thr Gly Ile Ser Leu Asn Ile
                485                 490                 495

Ser Ser Pro Gln Asn Glu Val Tyr Thr Met Arg Ile Arg Tyr Ala Ser
                500                 505                 510

Arg Gly Asn Gly Gln Leu Arg Leu Thr Thr Tyr Gln Tyr Ser Gly Tyr
                515                 520                 525

Ala Pro Arg Ile Val Asn Phe Asn Ala Thr Asp Ser Ser Gly Ser Leu
                530                 535                 540

Lys Phe Asn Ser Phe Asn Tyr Leu Thr Ile Gly Asn Val Ala Ala Asp
545                 550                 555                 560

Pro Thr Ala Leu Pro Arg Phe Val Phe Asp Leu Tyr Ser Gly Ser Pro
                565                 570                 575

Ile Ile Ile Asp Lys Ile Glu Phe Leu Pro Arg Gly Ile Ile
                580                 585                 590

<210> SEQ ID NO 12
<211> LENGTH: 1370
<212> TYPE: PRT
<213> ORGANISM: Bacillus thuringiensis

<400> SEQUENCE: 12

Val Lys Glu Ser Glu Ala Lys Lys Gly Gly Leu Arg Met Asn Gln
1               5                   10                  15

Asn Tyr Asn Asn Asn Glu Tyr Glu Ile Leu Asp Met Asn Asn Ser Gly
                20                  25                  30

Tyr Arg Ser Arg Tyr Pro Leu Ala Asn Ala Pro Gly Ser Glu Phe Gln
            35                  40                  45

Gln Met Asn Tyr Lys Asp Trp Met Asp Met Cys Thr Arg Gly Glu Ser
        50                  55                  60

Gly Glu Leu Phe Ser Ser Ala Arg Asn Gly Val Ile Ile Ala Thr Gly
65                  70                  75                  80

Ile Gly Trp Ala Ile Leu Gly Phe Val Pro Val Ile Gly Pro Gly Leu
                85                  90                  95

Ser Ala Ile Ser Gly Leu Leu Asn Val Leu Val Pro Phe Leu Trp Pro
                100                 105                 110

Glu Glu Gln Glu Thr Ser Gln Pro Gln Phe Thr Trp Gln Gln Leu Met
                115                 120                 125

Asn Ala Val Glu Glu Leu Ile Asp Gln Arg Ile Asp Ala Leu Ile Arg
            130                 135                 140

Ser Arg Ala Ile Glu Thr Thr Arg Ile Leu Gln Ser Arg Ile Arg Asp
145                 150                 155                 160

Tyr Gln Gln Ala Ile Cys Asn Leu Lys Thr Asp Pro Asn Asn Glu Ala
                165                 170                 175

Tyr Lys Ala Asp Val Arg Arg Glu Phe Asn Ala Asp Gln Ala
                180                 185                 190

Lys Ala Ala Ile Ile Gln Phe Asn Pro Arg Asn Pro Asp Gly Thr Glu
            195                 200                 205

Asp Ala Lys His Asn Ile Leu Leu Leu Ala Asp Tyr Ala Gln Ala Ala
        210                 215                 220
```

-continued

```
Asn Val His Leu Leu Leu Arg Asp Val Val Gln Phe Gly Glu Ser
225                 230                 235                 240

Trp Gly Phe Ser Pro Leu Glu Ile Gln Gln Tyr Tyr Ser Asn Thr Thr
            245                 250                 255

Ser Val Gly Asn Pro Gly Met Leu Gln Leu Leu Ala Asn Tyr Thr Asn
        260                 265                 270

His Cys Val Arg Trp Tyr Asn Ala Gly Leu Ala Thr Phe Asn Ser Tyr
    275                 280                 285

Leu Gln Trp Gln Glu Leu Asn Thr Phe Arg Arg Asp Met Thr Ile Met
290                 295                 300

Val Leu Asp Ile Ala Ser Leu Trp Pro Thr Tyr Asp Pro Lys Ser Tyr
305                 310                 315                 320

Pro Val Ile Ala Lys Ser Gln Leu Thr Arg Val Leu Tyr Thr Pro Ala
                325                 330                 335

Ile Gly Asn Asp Thr Asp Phe Glu Lys Leu Leu Pro Pro Ser Leu
            340                 345                 350

Phe Ser Trp Leu Arg Glu Ala Ile Phe Tyr Thr Pro Asn Pro Val Tyr
        355                 360                 365

Arg Met Glu Tyr Val Lys Tyr Thr Leu Val Leu Gln Lys Thr Leu Ser
370                 375                 380

Asn Asp Arg Tyr Glu Gln Thr Tyr Gly Ser Asn Phe Gly Ala Asp Ile
385                 390                 395                 400

Ala Tyr Ser Val Lys Ile Gly Thr Ala Pro Asn Ser Glu Val Tyr Arg
                405                 410                 415

Met His Thr Asn Ala Val Ile Tyr Ser Asn Asp Asn Ala Ser Leu Gly
            420                 425                 430

Lys Ile Thr Phe His Phe Ser Pro Ser Gly Thr Ser Glu Ser Val Gly
            435                 440                 445

Arg Glu Ile Val Gly Thr Gly Ile Asp Gln Gly Phe Ala Cys Arg Ser
450                 455                 460

Asn Leu Asn Glu Pro Cys Asp Pro Cys Val Thr Ala Cys Glu Val Gly
465                 470                 475                 480

Ser Val Asn Ala Ser Leu Pro Cys Asp Ser Pro Ser Leu Tyr Ser Glu
                485                 490                 495

Arg Leu Ser Trp Ile Ser Gly Glu Ile Leu Arg Ser Val Asn Phe Ser
            500                 505                 510

Ala Leu Asn Asn Ile Ala Tyr Gly Trp Thr His Val Ser Ala Asp Ala
            515                 520                 525

Asn Asn Leu Ile Ser Ala Glu Gln Ile Thr Gln Ile Pro Ala Val Lys
530                 535                 540

Ala Tyr Glu Leu Ser Gly Asp Ala Leu Val Ile Lys Gly Pro Gly Ser
545                 550                 555                 560

Thr Gly Gly Asp Leu Val Gln Leu Ser Ser Gly Ala Glu Thr Gly Gln
                565                 570                 575

Met Ala Met Trp Ile Thr Thr Pro Gln Gly Ser His Arg Tyr Arg Val
            580                 585                 590

Arg Ile Arg Tyr Ala Ser Ser Met Gln Thr Asn Leu Glu Ile Phe Met
            595                 600                 605

Thr Gly Ala Phe Gly Glu Phe Ser Ala Pro Ala Thr Thr Thr Asp Thr
610                 615                 620

Thr Asn Leu Thr Tyr Asp Lys Phe Gly Tyr Leu Glu Thr Val Leu Tyr
625                 630                 635                 640
```

-continued

```
Ser Tyr Ala His Val Glu Glu Ser Thr Glu His Ile Arg Met Tyr Ala
                645                 650                 655

Thr Gly Ser Gly Ser Gly Ser Phe Ile Leu Asp Lys Ile Glu Phe Ile
            660                 665                 670

Pro Ile Glu Gly Ser Leu Glu Ala Tyr Gln Ala Asp Gln Asp Val Glu
        675                 680                 685

Lys Ala Arg Lys Ala Val Asn Ala Leu Phe Thr Gly Asp Ala Lys Asn
    690                 695                 700

Ala Leu Lys Leu Asn Val Thr Asp Tyr Ala Val Asp Gln Ala Ala Asn
705                 710                 715                 720

Leu Val Glu Cys Val Ser Glu Asp Phe His Ala Gln Glu Lys Met Ile
                725                 730                 735

Leu Leu Asp Gln Val Lys Leu Ala Lys Arg Leu Ser Gln Ala Arg Asn
            740                 745                 750

Leu Leu Asn Tyr Gly Asp Phe Glu Ser Pro Asp Trp Ser Gly Glu Asn
        755                 760                 765

Gly Trp Lys Thr Ser Pro His Val His Val Ala Ser Asp Asn Pro Ile
    770                 775                 780

Phe Lys Gly His Tyr Leu His Met Pro Gly Ala Asn Gln Pro Gln Met
785                 790                 795                 800

Ser Asp Thr Ile Tyr Pro Thr Tyr Ile Tyr Gln Lys Val Asp Glu Ser
                805                 810                 815

Lys Leu Lys Ser Tyr Thr Arg Tyr His Val Arg Gly Phe Val Gly Asn
            820                 825                 830

Ser Lys Asn Leu Glu Leu Phe Val Glu Arg Tyr Gly Lys Glu Val His
        835                 840                 845

Val Glu Met Asp Val Pro Asn Asp Ile Arg Tyr Thr Leu Pro Met Asn
    850                 855                 860

Glu Cys Gly Gly Phe Asp Arg Cys Gly His Ser Ser Tyr Gln Ala Gly
865                 870                 875                 880

Thr Asp Ser Arg Thr Cys Thr Cys Lys Asp Thr Ala Arg Met Asp Ala
                885                 890                 895

Glu Cys Gln Cys Lys Asp Gln Pro Lys Arg Thr Ala Ser Gly Val Tyr
            900                 905                 910

Thr Asn Ala Tyr Ala Gly Asn Asp Arg Met Tyr Pro Asp Gly Tyr His
        915                 920                 925

Ala His Lys Ser Cys Gly Cys Asn Lys Lys Gly Gly Tyr Pro Asn Gly
    930                 935                 940

Lys His Ala His Lys Ser Cys Gly Cys Lys Asp Pro His Val Phe Ser
945                 950                 955                 960

Phe His Ile Asp Thr Gly Cys Val Asp Val Glu Glu Asn Ala Gly Leu
                965                 970                 975

Leu Phe Ala Leu Lys Ile Ala Ser Thr Asp Gly Leu Ala Asn Ile Asp
            980                 985                 990

Asn Leu Glu Ile Ile Glu Gly Gln Pro Leu Thr Gly Glu Ala Leu Ala
        995                 1000                1005

Arg Val Lys Lys Arg Glu His Arg Trp Lys Glu Glu Met Lys Gln
    1010                1015                1020

Lys Arg Cys Lys Thr Lys Glu Thr Val Glu Ala Ala Leu Thr Ala
    1025                1030                1035

Ile Asn Ala Leu Phe Thr Asn Lys Gln Tyr Asn Arg Leu Lys Phe
    1040                1045                1050

Asp Thr Leu Phe Pro His Ile Leu His Thr Asp Glu Leu Val Gln
```

Arg Ile Pro Tyr Val Tyr His Pro Phe Leu Gln Asp Ala Tyr Pro
    1070                1075                1080

Asp Val Pro Gly Met Asn Tyr Ala Ile Phe Gln Gln Leu Ser Ser
    1085                1090                1095

Met Ile Asn Arg Ala Arg Gly Leu Tyr Asp Met Arg Asn Leu Val
    1100                1105                1110

Gln Asn Gly Thr Phe Ser Ser Gly Ala Gly Ser Trp His Val Thr
    1115                1120                1125

Asp Gly Val Asn Thr Gln Pro Glu Gly Asn Thr Ser Val Leu Val
    1130                1135                1140

Leu Arg Glu Trp Ser Asp Lys Ala Val Gln Asn Leu Arg Ile Asp
    1145                1150                1155

Glu Glu Arg Gly Tyr Val Leu Arg Val Thr Ala Arg Lys Glu Gly
    1160                1165                1170

Asn Gly Asp Gly Tyr Val Val Ile His Asp Cys Asp Asn Gln Met
    1175                1180                1185

Glu Lys Leu Thr Phe Thr Ala Cys Asp Tyr Ser Thr Thr Arg Ala
    1190                1195                1200

Ser Thr Gly Thr Gln Ala Thr Val Ile Pro Val Thr Asn Cys Pro
    1205                1210                1215

Pro Cys His Ser Gly Thr Trp Gly Glu Arg Pro Thr Pro Ile
    1220                1225                1230

Thr Met Leu Thr Gly Tyr Val Thr Lys Thr Ala Glu Ile Phe Pro
    1235                1240                1245

Asp Thr Asp Arg Ile Arg Ile Glu Ile Gly Glu Thr Glu Gly Thr
    1250                1255                1260

Phe Lys Ile Glu Ser Val Glu Leu Ile Cys Met Glu His Met Glu
    1265                1270                1275

Asp His Met Tyr Asp Met Ala Gly Asn Leu Glu Glu Glu Met Gln
    1280                1285                1290

Gly Leu Gly Ile Glu Ser Ser His Ala Val Thr His Glu Met Cys
    1295                1300                1305

Phe Ser Trp Asp Ile Met Cys Pro Met Glu Ala Ser Ile Pro Pro
    1310                1315                1320

Ile Val Pro Pro Thr Asn Met Tyr Asp Met Ala Gly Asn Val Glu
    1325                1330                1335

Glu Glu Met Lys Tyr Leu Lys Pro Ser Ser Met Ala Ser Thr Leu
    1340                1345                1350

Asp Pro Ile Cys Tyr Thr Lys Ile Gly Glu Phe Gly Cys Pro Leu
    1355                1360                1365

Asn Gln
    1370

<210> SEQ ID NO 13
<211> LENGTH: 681
<212> TYPE: PRT
<213> ORGANISM: Bacillus thuringiensis

<400> SEQUENCE: 13

Val Lys Glu Ser Glu Glu Ala Lys Lys Gly Gly Leu Arg Met Asn Gln
1               5                   10                  15

Asn Tyr Asn Asn Glu Tyr Glu Ile Leu Asp Met Asn Asn Ser Gly
            20                  25                  30

-continued

```
Tyr Arg Ser Arg Tyr Pro Leu Ala Asn Ala Pro Gly Ser Glu Phe Gln
         35                  40                  45

Gln Met Asn Tyr Lys Asp Trp Met Asp Met Cys Thr Arg Gly Glu Ser
 50                  55                  60

Gly Glu Leu Phe Ser Ser Ala Arg Asn Gly Val Ile Ile Ala Thr Gly
 65                  70                  75                  80

Ile Gly Trp Ala Ile Leu Gly Phe Val Pro Val Ile Gly Pro Gly Leu
                 85                  90                  95

Ser Ala Ile Ser Gly Leu Leu Asn Val Leu Pro Phe Leu Trp Pro
             100                 105                 110

Glu Glu Gln Glu Thr Ser Gln Pro Gln Phe Thr Trp Gln Gln Leu Met
         115                 120                 125

Asn Ala Val Glu Glu Leu Ile Asp Gln Arg Ile Asp Ala Leu Ile Arg
130                 135                 140

Ser Arg Ala Ile Glu Thr Thr Arg Ile Leu Gln Ser Arg Ile Arg Asp
145                 150                 155                 160

Tyr Gln Gln Ala Ile Cys Asn Leu Lys Thr Asp Pro Asn Asn Glu Ala
                 165                 170                 175

Tyr Lys Ala Asp Val Arg Arg Glu Phe Asn Asp Ala Asp Gln Ala
             180                 185                 190

Lys Ala Ala Ile Ile Gln Phe Asn Pro Arg Asn Pro Asp Gly Thr Glu
        195                 200                 205

Asp Ala Lys His Asn Ile Leu Leu Ala Asp Tyr Ala Gln Ala Ala
        210                 215                 220

Asn Val His Leu Leu Leu Arg Asp Val Val Gln Phe Gly Glu Ser
225                 230                 235                 240

Trp Gly Phe Ser Pro Leu Glu Ile Gln Gln Tyr Tyr Ser Asn Thr Thr
                 245                 250                 255

Ser Val Gly Asn Pro Gly Met Leu Gln Leu Leu Ala Asn Tyr Thr Asn
             260                 265                 270

His Cys Val Arg Trp Tyr Asn Ala Gly Leu Ala Thr Phe Asn Ser Tyr
        275                 280                 285

Leu Gln Trp Gln Glu Leu Asn Thr Phe Arg Arg Asp Met Thr Ile Met
        290                 295                 300

Val Leu Asp Ile Ala Ser Leu Trp Pro Thr Tyr Asp Pro Lys Ser Tyr
305                 310                 315                 320

Pro Val Ile Ala Lys Ser Gln Leu Thr Arg Val Leu Tyr Thr Pro Ala
                 325                 330                 335

Ile Gly Asn Asp Thr Asp Phe Glu Lys Leu Pro Pro Pro Ser Leu
             340                 345                 350

Phe Ser Trp Leu Arg Glu Ala Ile Phe Tyr Thr Pro Asn Pro Val Tyr
        355                 360                 365

Arg Met Glu Tyr Val Lys Tyr Thr Leu Val Leu Gln Lys Thr Leu Ser
        370                 375                 380

Asn Asp Arg Tyr Glu Gln Thr Tyr Gly Ser Asn Phe Gly Ala Asp Ile
385                 390                 395                 400

Ala Tyr Ser Val Lys Ile Gly Thr Ala Pro Asn Ser Glu Val Tyr Arg
                 405                 410                 415

Met His Thr Asn Ala Val Ile Tyr Ser Asn Asp Asn Ala Ser Leu Gly
             420                 425                 430

Lys Ile Thr Phe His Phe Ser Pro Ser Gly Thr Ser Glu Ser Val Gly
        435                 440                 445

Arg Glu Ile Val Gly Thr Gly Ile Asp Gln Gly Phe Ala Cys Arg Ser
```

```
            450                 455                 460
Asn Leu Asn Glu Pro Cys Asp Pro Cys Val Thr Ala Cys Glu Val Gly
465                 470                 475                 480

Ser Val Asn Ala Ser Leu Pro Cys Asp Ser Pro Ser Leu Tyr Ser Glu
                485                 490                 495

Arg Leu Ser Trp Ile Ser Gly Glu Ile Leu Arg Ser Val Asn Phe Ser
            500                 505                 510

Ala Leu Asn Asn Ile Ala Tyr Gly Trp Thr His Val Ser Ala Asp Ala
            515                 520                 525

Asn Asn Leu Ile Ser Ala Glu Gln Ile Thr Gln Ile Pro Ala Val Lys
        530                 535                 540

Ala Tyr Glu Leu Ser Gly Asp Ala Leu Val Ile Lys Gly Pro Gly Ser
545                 550                 555                 560

Thr Gly Gly Asp Leu Val Gln Leu Ser Ser Gly Ala Glu Thr Gly Gln
                565                 570                 575

Met Ala Met Trp Ile Thr Thr Pro Gln Gly Ser His Arg Tyr Arg Val
            580                 585                 590

Arg Ile Arg Tyr Ala Ser Ser Met Gln Thr Asn Leu Glu Ile Phe Met
        595                 600                 605

Thr Gly Ala Phe Gly Glu Phe Ser Ala Pro Ala Thr Thr Thr Asp Thr
        610                 615                 620

Thr Asn Leu Thr Tyr Asp Lys Phe Gly Tyr Leu Glu Thr Val Leu Tyr
625                 630                 635                 640

Ser Tyr Ala His Val Glu Glu Ser Thr Glu His Ile Arg Met Tyr Ala
                645                 650                 655

Thr Gly Ser Gly Ser Gly Ser Phe Ile Leu Asp Lys Ile Glu Phe Ile
            660                 665                 670

Pro Ile Glu Gly Ser Leu Glu Ala Tyr
            675                 680

<210> SEQ ID NO 14
<211> LENGTH: 668
<212> TYPE: PRT
<213> ORGANISM: Bacillus thuringiensis

<400> SEQUENCE: 14

Met Asn Gln Asn Tyr Asn Asn Glu Tyr Glu Ile Leu Asp Met Asn
1               5                   10                  15

Asn Ser Gly Tyr Arg Ser Arg Tyr Pro Leu Ala Asn Ala Pro Gly Ser
                20                  25                  30

Glu Phe Gln Gln Met Asn Tyr Lys Asp Trp Met Asp Met Cys Thr Arg
            35                  40                  45

Gly Glu Ser Gly Glu Leu Phe Ser Ser Ala Arg Asn Gly Val Ile Ile
        50                  55                  60

Ala Thr Gly Ile Gly Trp Ala Ile Leu Gly Phe Val Pro Val Ile Gly
65                  70                  75                  80

Pro Gly Leu Ser Ala Ile Ser Gly Leu Leu Asn Val Leu Val Pro Phe
                85                  90                  95

Leu Trp Pro Glu Glu Gln Glu Thr Ser Gln Pro Gln Phe Thr Trp Gln
            100                 105                 110

Gln Leu Met Asn Ala Val Glu Glu Leu Ile Asp Gln Arg Ile Asp Ala
        115                 120                 125

Leu Ile Arg Ser Arg Ala Ile Glu Thr Thr Arg Ile Leu Gln Ser Arg
    130                 135                 140
```

-continued

Ile Arg Asp Tyr Gln Gln Ala Ile Cys Asn Leu Lys Thr Asp Pro Asn
145                 150                 155                 160

Asn Glu Ala Tyr Lys Ala Asp Val Arg Arg Glu Phe Asn Asp Ala Asp
                165                 170                 175

Asp Gln Ala Lys Ala Ala Ile Ile Gln Phe Asn Pro Arg Asn Pro Asp
                180                 185                 190

Gly Thr Glu Asp Ala Lys His Asn Ile Leu Leu Ala Asp Tyr Ala
                195                 200                 205

Gln Ala Ala Asn Val His Leu Leu Leu Arg Asp Val Val Gln Phe
210                 215                 220

Gly Glu Ser Trp Gly Phe Ser Pro Leu Glu Ile Gln Gln Tyr Tyr Ser
225                 230                 235                 240

Asn Thr Thr Ser Val Gly Asn Pro Gly Met Leu Gln Leu Leu Ala Asn
                245                 250                 255

Tyr Thr Asn His Cys Val Arg Trp Tyr Asn Ala Gly Leu Ala Thr Phe
                260                 265                 270

Asn Ser Tyr Leu Gln Trp Gln Glu Leu Asn Thr Phe Arg Arg Asp Met
                275                 280                 285

Thr Ile Met Val Leu Asp Ile Ala Ser Leu Trp Pro Thr Tyr Asp Pro
290                 295                 300

Lys Ser Tyr Pro Val Ile Ala Lys Ser Gln Leu Thr Arg Val Leu Tyr
305                 310                 315                 320

Thr Pro Ala Ile Gly Asn Asp Thr Asp Phe Glu Lys Leu Leu Pro Pro
                325                 330                 335

Pro Ser Leu Phe Ser Trp Leu Arg Glu Ala Ile Phe Tyr Thr Pro Asn
                340                 345                 350

Pro Val Tyr Arg Met Glu Tyr Val Lys Tyr Thr Leu Val Leu Gln Lys
                355                 360                 365

Thr Leu Ser Asn Asp Arg Tyr Glu Gln Thr Tyr Gly Ser Asn Phe Gly
                370                 375                 380

Ala Asp Ile Ala Tyr Ser Val Lys Ile Gly Thr Ala Pro Asn Ser Glu
385                 390                 395                 400

Val Tyr Arg Met His Thr Asn Ala Val Ile Tyr Ser Asn Asp Asn Ala
                405                 410                 415

Ser Leu Gly Lys Ile Thr Phe His Phe Ser Pro Ser Gly Thr Ser Glu
                420                 425                 430

Ser Val Gly Arg Glu Ile Val Gly Thr Gly Ile Asp Gln Gly Phe Ala
                435                 440                 445

Cys Arg Ser Asn Leu Asn Glu Pro Cys Asp Pro Cys Val Thr Ala Cys
450                 455                 460

Glu Val Gly Ser Val Asn Ala Ser Leu Pro Cys Asp Ser Pro Ser Leu
465                 470                 475                 480

Tyr Ser Glu Arg Leu Ser Trp Ile Ser Gly Glu Ile Leu Arg Ser Val
                485                 490                 495

Asn Phe Ser Ala Leu Asn Asn Ile Ala Tyr Gly Trp Thr His Val Ser
                500                 505                 510

Ala Asp Ala Asn Asn Leu Ile Ser Ala Glu Gln Ile Thr Gln Ile Pro
                515                 520                 525

Ala Val Lys Ala Tyr Glu Leu Ser Gly Asp Ala Leu Val Ile Lys Gly
                530                 535                 540

Pro Gly Ser Thr Gly Gly Asp Leu Val Gln Leu Ser Ser Gly Ala Glu
545                 550                 555                 560

Thr Gly Gln Met Ala Met Trp Ile Thr Thr Pro Gln Gly Ser His Arg 565 570 575

Tyr Arg Val Arg Ile Arg Tyr Ala Ser Ser Met Gln Thr Asn Leu Glu
580 585 590

Ile Phe Met Thr Gly Ala Phe Gly Glu Phe Ser Ala Pro Ala Thr Thr
595 600 605

Thr Asp Thr Thr Asn Leu Thr Tyr Asp Lys Phe Gly Tyr Leu Glu Thr
610 615 620

Val Leu Tyr Ser Tyr Ala His Val Glu Glu Ser Thr Glu His Ile Arg
625 630 635 640

Met Tyr Ala Thr Gly Ser Gly Ser Gly Ser Phe Ile Leu Asp Lys Ile
645 650 655

Glu Phe Ile Pro Ile Glu Gly Ser Leu Glu Ala Tyr
660 665

<210> SEQ ID NO 15
<211> LENGTH: 654
<212> TYPE: PRT
<213> ORGANISM: Bacillus thuringiensis

<400> SEQUENCE: 15

Met Asn Asn Ser Gly Tyr Arg Ser Arg Tyr Pro Leu Ala Asn Ala Pro
1 5 10 15

Gly Ser Glu Phe Gln Gln Met Asn Tyr Lys Asp Trp Met Asp Met Cys
20 25 30

Thr Arg Gly Glu Ser Gly Glu Leu Phe Ser Ser Ala Arg Asn Gly Val
35 40 45

Ile Ile Ala Thr Gly Ile Gly Trp Ala Ile Leu Gly Phe Val Pro Val
50 55 60

Ile Gly Pro Gly Leu Ser Ala Ile Ser Gly Leu Leu Asn Val Leu Val
65 70 75 80

Pro Phe Leu Trp Pro Glu Glu Gln Glu Thr Ser Gln Pro Gln Phe Thr
85 90 95

Trp Gln Gln Leu Met Asn Ala Val Glu Glu Leu Ile Asp Gln Arg Ile
100 105 110

Asp Ala Leu Ile Arg Ser Arg Ala Ile Glu Thr Thr Arg Ile Leu Gln
115 120 125

Ser Arg Ile Arg Asp Tyr Gln Gln Ala Ile Cys Asn Leu Lys Thr Asp
130 135 140

Pro Asn Asn Glu Ala Tyr Lys Ala Asp Val Arg Arg Glu Phe Asn Asp
145 150 155 160

Ala Asp Asp Gln Ala Lys Ala Ala Ile Ile Gln Phe Asn Pro Arg Asn
165 170 175

Pro Asp Gly Thr Glu Asp Ala Lys His Asn Ile Leu Leu Leu Ala Asp
180 185 190

Tyr Ala Gln Ala Ala Asn Val His Leu Leu Leu Leu Arg Asp Val Val
195 200 205

Gln Phe Gly Glu Ser Trp Gly Phe Ser Pro Leu Glu Ile Gln Gln Tyr
210 215 220

Tyr Ser Asn Thr Thr Ser Val Gly Asn Pro Gly Met Leu Gln Leu Leu
225 230 235 240

Ala Asn Tyr Thr Asn His Cys Val Arg Trp Tyr Asn Ala Gly Leu Ala
245 250 255

Thr Phe Asn Ser Tyr Leu Gln Trp Gln Glu Leu Asn Thr Phe Arg Arg
260 265 270

Asp Met Thr Ile Met Val Leu Asp Ile Ala Ser Leu Trp Pro Thr Tyr
275                 280                 285

Asp Pro Lys Ser Tyr Pro Val Ile Ala Lys Ser Gln Leu Thr Arg Val
290                 295                 300

Leu Tyr Thr Pro Ala Ile Gly Asn Asp Thr Asp Phe Glu Lys Leu Leu
305                 310                 315                 320

Pro Pro Pro Ser Leu Phe Ser Trp Leu Arg Glu Ala Ile Phe Tyr Thr
                325                 330                 335

Pro Asn Pro Val Tyr Arg Met Glu Tyr Val Lys Tyr Thr Leu Val Leu
                340                 345                 350

Gln Lys Thr Leu Ser Asn Asp Arg Tyr Glu Gln Thr Tyr Gly Ser Asn
355                 360                 365

Phe Gly Ala Asp Ile Ala Tyr Ser Val Lys Ile Gly Thr Ala Pro Asn
370                 375                 380

Ser Glu Val Tyr Arg Met His Thr Asn Ala Val Ile Tyr Ser Asn Asp
385                 390                 395                 400

Asn Ala Ser Leu Gly Lys Ile Thr Phe His Phe Ser Pro Ser Gly Thr
                405                 410                 415

Ser Glu Ser Val Gly Arg Glu Ile Val Gly Thr Gly Ile Asp Gln Gly
                420                 425                 430

Phe Ala Cys Arg Ser Asn Leu Asn Glu Pro Cys Asp Pro Cys Val Thr
                435                 440                 445

Ala Cys Glu Val Gly Ser Val Asn Ala Ser Leu Pro Cys Asp Ser Pro
450                 455                 460

Ser Leu Tyr Ser Glu Arg Leu Ser Trp Ile Ser Gly Glu Ile Leu Arg
465                 470                 475                 480

Ser Val Asn Phe Ser Ala Leu Asn Asn Ile Ala Tyr Gly Trp Thr His
                485                 490                 495

Val Ser Ala Asp Ala Asn Asn Leu Ile Ser Ala Glu Gln Ile Thr Gln
                500                 505                 510

Ile Pro Ala Val Lys Ala Tyr Glu Leu Ser Gly Asp Ala Leu Val Ile
                515                 520                 525

Lys Gly Pro Gly Ser Thr Gly Gly Asp Leu Val Gln Leu Ser Ser Gly
530                 535                 540

Ala Glu Thr Gly Gln Met Ala Met Trp Ile Thr Thr Pro Gln Gly Ser
545                 550                 555                 560

His Arg Tyr Arg Val Arg Ile Arg Tyr Ala Ser Ser Met Gln Thr Asn
                565                 570                 575

Leu Glu Ile Phe Met Thr Gly Ala Phe Gly Glu Phe Ser Ala Pro Ala
                580                 585                 590

Thr Thr Thr Asp Thr Thr Asn Leu Thr Tyr Asp Lys Phe Gly Tyr Leu
                595                 600                 605

Glu Thr Val Leu Tyr Ser Tyr Ala His Val Glu Glu Ser Thr Glu His
610                 615                 620

Ile Arg Met Tyr Ala Thr Gly Ser Gly Ser Gly Ser Phe Ile Leu Asp
625                 630                 635                 640

Lys Ile Glu Phe Ile Pro Ile Glu Gly Ser Leu Glu Ala Tyr
                645                 650

<210> SEQ ID NO 16
<211> LENGTH: 632
<212> TYPE: PRT
<213> ORGANISM: Bacillus thuringiensis

<400> SEQUENCE: 16

-continued

```
Met Asn Tyr Lys Asp Trp Met Asp Met Cys Thr Arg Gly Glu Ser Gly
1               5                   10                  15

Glu Leu Phe Ser Ser Ala Arg Asn Gly Val Ile Ile Ala Thr Gly Ile
            20                  25                  30

Gly Trp Ala Ile Leu Gly Phe Val Pro Val Ile Gly Pro Gly Leu Ser
        35                  40                  45

Ala Ile Ser Gly Leu Leu Asn Val Leu Val Pro Phe Leu Trp Pro Glu
    50                  55                  60

Glu Gln Glu Thr Ser Gln Pro Gln Phe Thr Trp Gln Gln Leu Met Asn
65              70                  75                  80

Ala Val Glu Glu Leu Ile Asp Gln Arg Ile Ala Leu Ile Arg Ser
                85                  90                  95

Arg Ala Ile Glu Thr Thr Arg Ile Leu Gln Ser Arg Ile Arg Asp Tyr
                100                 105                 110

Gln Gln Ala Ile Cys Asn Leu Lys Thr Asp Pro Asn Asn Glu Ala Tyr
            115                 120                 125

Lys Ala Asp Val Arg Arg Glu Phe Asn Asp Ala Asp Gln Ala Lys
130                 135                 140

Ala Ala Ile Ile Gln Phe Asn Pro Arg Asn Pro Asp Gly Thr Glu Asp
145                 150                 155                 160

Ala Lys His Asn Ile Leu Leu Leu Ala Asp Tyr Ala Gln Ala Ala Asn
                165                 170                 175

Val His Leu Leu Leu Leu Arg Asp Val Val Gln Phe Gly Glu Ser Trp
            180                 185                 190

Gly Phe Ser Pro Leu Glu Ile Gln Gln Tyr Tyr Ser Asn Thr Thr Ser
        195                 200                 205

Val Gly Asn Pro Gly Met Leu Gln Leu Leu Ala Asn Tyr Thr Asn His
    210                 215                 220

Cys Val Arg Trp Tyr Asn Ala Gly Leu Ala Thr Phe Asn Ser Tyr Leu
225                 230                 235                 240

Gln Trp Gln Glu Leu Asn Thr Phe Arg Arg Asp Met Thr Ile Met Val
            245                 250                 255

Leu Asp Ile Ala Ser Leu Trp Pro Thr Tyr Asp Pro Lys Ser Tyr Pro
                260                 265                 270

Val Ile Ala Lys Ser Gln Leu Thr Arg Val Leu Tyr Thr Pro Ala Ile
            275                 280                 285

Gly Asn Asp Thr Asp Phe Glu Lys Leu Leu Pro Pro Pro Ser Leu Phe
        290                 295                 300

Ser Trp Leu Arg Glu Ala Ile Phe Tyr Thr Pro Asn Pro Val Tyr Arg
305                 310                 315                 320

Met Glu Tyr Val Lys Tyr Thr Leu Val Leu Gln Lys Thr Leu Ser Asn
                325                 330                 335

Asp Arg Tyr Glu Gln Thr Tyr Gly Ser Asn Phe Gly Ala Asp Ile Ala
            340                 345                 350

Tyr Ser Val Lys Ile Gly Thr Ala Pro Asn Ser Glu Val Tyr Arg Met
        355                 360                 365

His Thr Asn Ala Val Ile Tyr Ser Asn Asp Asn Ala Ser Leu Gly Lys
    370                 375                 380

Ile Thr Phe His Phe Ser Pro Ser Gly Thr Ser Glu Ser Val Gly Arg
385                 390                 395                 400

Glu Ile Val Gly Thr Gly Ile Asp Gln Gly Phe Ala Cys Arg Ser Asn
                405                 410                 415
```

```
Leu Asn Glu Pro Cys Asp Pro Cys Val Thr Ala Cys Glu Val Gly Ser
                420                 425                 430

Val Asn Ala Ser Leu Pro Cys Asp Ser Pro Ser Leu Tyr Ser Glu Arg
            435                 440                 445

Leu Ser Trp Ile Ser Gly Glu Ile Leu Arg Ser Val Asn Phe Ser Ala
        450                 455                 460

Leu Asn Ile Ala Tyr Gly Trp Thr His Val Ser Ala Asp Ala Asn
465                 470                 475                 480

Asn Leu Ile Ser Ala Glu Gln Ile Thr Gln Ile Pro Ala Val Lys Ala
                485                 490                 495

Tyr Glu Leu Ser Gly Asp Ala Leu Val Ile Lys Gly Pro Gly Ser Thr
            500                 505                 510

Gly Gly Asp Leu Val Gln Leu Ser Ser Gly Ala Glu Thr Gly Gln Met
        515                 520                 525

Ala Met Trp Ile Thr Thr Pro Gln Gly Ser His Arg Tyr Arg Val Arg
        530                 535                 540

Ile Arg Tyr Ala Ser Ser Met Gln Thr Asn Leu Glu Ile Phe Met Thr
545                 550                 555                 560

Gly Ala Phe Gly Glu Phe Ser Ala Pro Ala Thr Thr Asp Thr Thr
            565                 570                 575

Asn Leu Thr Tyr Asp Lys Phe Gly Tyr Leu Glu Thr Val Leu Tyr Ser
                580                 585                 590

Tyr Ala His Val Glu Glu Ser Thr Glu His Ile Arg Met Tyr Ala Thr
            595                 600                 605

Gly Ser Gly Ser Gly Ser Phe Ile Leu Asp Lys Ile Glu Phe Ile Pro
        610                 615                 620

Ile Glu Gly Ser Leu Glu Ala Tyr
625                 630

<210> SEQ ID NO 17
<211> LENGTH: 668
<212> TYPE: PRT
<213> ORGANISM: Bacillus thuringiensis

<400> SEQUENCE: 17

Met Asn Gln Asn Tyr Asn Asn Glu Tyr Glu Ile Leu Asp Met Asn
1               5                   10                  15

Asn Ser Gly Tyr Arg Ser Arg Tyr Pro Leu Ala Asn Ala Pro Gly Ser
            20                  25                  30

Glu Phe Gln Gln Met Asn Tyr Lys Asp Trp Met Asp Met Cys Thr Arg
        35                  40                  45

Gly Glu Ser Gly Glu Leu Phe Ser Ser Ala Arg Asn Gly Val Ile Ile
    50                  55                  60

Ala Thr Gly Ile Gly Trp Ala Ile Leu Gly Phe Val Pro Val Ile Gly
65                  70                  75                  80

Pro Gly Leu Ser Ala Ile Ser Gly Leu Leu Asn Val Leu Val Pro Phe
                85                  90                  95

Leu Trp Pro Glu Glu Gln Glu Thr Ser Gln Pro Gln Phe Thr Trp Gln
            100                 105                 110

Gln Leu Met Asn Ala Val Glu Glu Leu Ile Asp Gln Arg Ile Asp Ala
        115                 120                 125

Leu Ile Arg Ser Arg Ala Ile Glu Thr Thr Arg Ile Leu Gln Ser Arg
    130                 135                 140

Ile Arg Asp Tyr Gln Gln Ala Ile Cys Asn Leu Lys Thr Asp Pro Asn
145                 150                 155                 160
```

```
Asn Glu Ala Tyr Lys Ala Asp Val Arg Arg Glu Phe Asn Asp Ala Asp
                165                 170                 175

Asp Gln Ala Lys Ala Ala Ile Ile Gln Phe Asn Pro Arg Asn Pro Asp
            180                 185                 190

Gly Thr Glu Asp Ala Lys His Asn Ile Leu Leu Leu Ala Asp Tyr Ala
        195                 200                 205

Gln Ala Ala Asn Val His Leu Leu Leu Leu Arg Asp Val Val Gln Phe
    210                 215                 220

Gly Glu Ser Trp Gly Phe Ser Pro Leu Glu Ile Gln Gln Tyr Tyr Ser
225                 230                 235                 240

Asn Thr Thr Ser Val Gly Asn Pro Gly Met Leu Gln Leu Leu Ala Asn
                245                 250                 255

Tyr Thr Asn His Cys Val Arg Trp Tyr Asn Ala Gly Leu Ala Thr Phe
            260                 265                 270

Asn Ser Tyr Leu Gln Trp Gln Glu Leu Asn Thr Phe Arg Arg Asp Met
        275                 280                 285

Thr Ile Met Val Leu Asp Ile Ala Ser Leu Trp Pro Thr Tyr Asp Pro
    290                 295                 300

Lys Ser Tyr Pro Val Ile Ala Lys Ser Gln Leu Thr Arg Val Leu Tyr
305                 310                 315                 320

Thr Pro Ala Ile Gly Asn Asp Thr Asp Phe Glu Lys Leu Leu Pro Pro
                325                 330                 335

Pro Ser Leu Phe Ser Trp Leu Arg Glu Ala Ile Phe Tyr Thr Pro Asn
            340                 345                 350

Pro Val Tyr Arg Met Glu Tyr Val Lys Tyr Thr Leu Val Leu Gln Lys
        355                 360                 365

Thr Leu Ser Asn Asp Arg Tyr Glu Gln Thr Tyr Gly Ser Asn Phe Gly
    370                 375                 380

Ala Asp Ile Ala Tyr Ser Val Lys Ile Gly Thr Ala Pro Asn Ser Glu
385                 390                 395                 400

Val Tyr Arg Met His Thr Asn Ala Val Ile Tyr Ser Asn Asp Asn Ala
                405                 410                 415

Ser Leu Gly Lys Ile Thr Phe His Phe Ser Pro Ser Gly Thr Ser Glu
            420                 425                 430

Ser Val Gly Arg Glu Ile Val Gly Thr Gly Ile Asp Gln Gly Phe Ala
        435                 440                 445

Cys Arg Ser Asn Leu Asn Glu Pro Cys Asp Pro Cys Val Thr Ala Cys
    450                 455                 460

Glu Val Gly Ser Val Asn Ala Ser Leu Pro Cys Asp Ser Pro Ser Leu
465                 470                 475                 480

Tyr Ser Glu Arg Leu Ser Trp Ile Ser Gly Glu Ile Leu Arg Ser Val
                485                 490                 495

Asn Phe Ser Ala Leu Asn Asn Ile Ala Tyr Gly Trp Thr His Val Ser
            500                 505                 510

Ala Asp Ala Asn Asn Leu Ile Ser Ala Glu Gln Ile Thr Gln Ile Pro
        515                 520                 525

Ala Val Lys Ala Tyr Glu Leu Ser Gly Asp Ala Leu Val Ile Lys Gly
    530                 535                 540

Pro Gly Ser Thr Gly Gly Asp Leu Val Gln Leu Ser Ser Gly Ala Glu
545                 550                 555                 560

Thr Gly Gln Met Ala Met Trp Ile Thr Thr Pro Gln Gly Ser His Arg
                565                 570                 575
```

```
Tyr Arg Val Arg Ile Arg Tyr Ala Ser Ser Met Gln Thr Asn Leu Glu
            580                 585                 590

Ile Phe Met Thr Gly Ala Phe Gly Glu Phe Ser Ala Pro Ala Thr Thr
        595                 600                 605

Thr Asp Thr Thr Asn Leu Thr Tyr Asp Lys Phe Gly Tyr Leu Glu Thr
    610                 615                 620

Val Leu Tyr Ser Tyr Ala His Val Glu Glu Ser Thr Glu His Ile Arg
625                 630                 635                 640

Met Tyr Ala Thr Gly Ser Gly Ser Gly Ser Phe Ile Leu Asp Lys Ile
                645                 650                 655

Glu Phe Ile Pro Ile Glu Gly Ser Leu Glu Ala Tyr
            660                 665

<210> SEQ ID NO 18
<211> LENGTH: 654
<212> TYPE: PRT
<213> ORGANISM: Bacillus thuringiensis

<400> SEQUENCE: 18

Met Asn Asn Ser Gly Tyr Arg Ser Arg Tyr Pro Leu Ala Asn Ala Pro
1               5                   10                  15

Gly Ser Glu Phe Gln Gln Met Asn Tyr Lys Asp Trp Met Asp Met Cys
            20                  25                  30

Thr Arg Gly Glu Ser Gly Glu Leu Phe Ser Ser Ala Arg Asn Gly Val
        35                  40                  45

Ile Ile Ala Thr Gly Ile Gly Trp Ala Ile Leu Gly Phe Val Pro Val
    50                  55                  60

Ile Gly Pro Gly Leu Ser Ala Ile Ser Gly Leu Leu Asn Val Leu Val
65                  70                  75                  80

Pro Phe Leu Trp Pro Glu Glu Gln Glu Thr Ser Gln Pro Gln Phe Thr
                85                  90                  95

Trp Gln Gln Leu Met Asn Ala Val Glu Glu Leu Ile Asp Gln Arg Ile
            100                 105                 110

Asp Ala Leu Ile Arg Ser Arg Ala Ile Glu Thr Thr Arg Ile Leu Gln
        115                 120                 125

Ser Arg Ile Arg Asp Tyr Gln Gln Ala Ile Cys Asn Leu Lys Thr Asp
    130                 135                 140

Pro Asn Asn Glu Ala Tyr Lys Ala Asp Val Arg Arg Glu Phe Asn Asp
145                 150                 155                 160

Ala Asp Asp Gln Ala Lys Ala Ala Ile Ile Gln Phe Asn Pro Arg Asn
                165                 170                 175

Pro Asp Gly Thr Glu Asp Ala Lys His Asn Ile Leu Leu Leu Ala Asp
            180                 185                 190

Tyr Ala Gln Ala Ala Asn Val His Leu Leu Leu Arg Asp Val Val
        195                 200                 205

Gln Phe Gly Glu Ser Trp Gly Phe Ser Pro Leu Glu Ile Gln Gln Tyr
    210                 215                 220

Tyr Ser Asn Thr Thr Ser Val Gly Asn Pro Gly Met Leu Gln Leu Leu
225                 230                 235                 240

Ala Asn Tyr Thr Asn His Cys Val Arg Trp Tyr Asn Ala Gly Leu Ala
                245                 250                 255

Thr Phe Asn Ser Tyr Leu Gln Trp Gln Glu Leu Asn Thr Phe Arg Arg
            260                 265                 270

Asp Met Thr Ile Met Val Leu Asp Ile Ala Ser Leu Trp Pro Thr Tyr
        275                 280                 285
```

```
Asp Pro Lys Ser Tyr Pro Val Ile Ala Lys Ser Gln Leu Thr Arg Val
    290                 295                 300

Leu Tyr Thr Pro Ala Ile Gly Asn Asp Thr Asp Phe Glu Lys Leu Leu
305                 310                 315                 320

Pro Pro Pro Ser Leu Phe Ser Trp Leu Arg Glu Ala Ile Phe Tyr Thr
                325                 330                 335

Pro Asn Pro Val Tyr Arg Met Glu Tyr Val Lys Tyr Thr Leu Val Leu
            340                 345                 350

Gln Lys Thr Leu Ser Asn Asp Arg Tyr Glu Gln Thr Tyr Gly Ser Asn
        355                 360                 365

Phe Gly Ala Asp Ile Ala Tyr Ser Val Lys Ile Gly Thr Ala Pro Asn
370                 375                 380

Ser Glu Val Tyr Arg Met His Thr Asn Ala Val Ile Tyr Ser Asn Asp
385                 390                 395                 400

Asn Ala Ser Leu Gly Lys Ile Thr Phe His Phe Ser Pro Ser Gly Thr
                405                 410                 415

Ser Glu Ser Val Gly Arg Glu Ile Val Gly Thr Gly Ile Asp Gln Gly
            420                 425                 430

Phe Ala Cys Arg Ser Asn Leu Asn Glu Pro Cys Asp Pro Cys Val Thr
        435                 440                 445

Ala Cys Glu Val Gly Ser Val Asn Ala Ser Leu Pro Cys Asp Ser Pro
450                 455                 460

Ser Leu Tyr Ser Glu Arg Leu Ser Trp Ile Ser Gly Glu Ile Leu Arg
465                 470                 475                 480

Ser Val Asn Phe Ser Ala Leu Asn Ile Ala Tyr Gly Trp Thr His
                485                 490                 495

Val Ser Ala Asp Ala Asn Asn Leu Ile Ser Ala Glu Gln Ile Thr Gln
            500                 505                 510

Ile Pro Ala Val Lys Ala Tyr Glu Leu Ser Gly Asp Ala Leu Val Ile
        515                 520                 525

Lys Gly Pro Gly Ser Thr Gly Gly Asp Leu Val Gln Leu Ser Ser Gly
530                 535                 540

Ala Glu Thr Gly Gln Met Ala Met Trp Ile Thr Thr Pro Gln Gly Ser
545                 550                 555                 560

His Arg Tyr Arg Val Arg Ile Arg Tyr Ala Ser Ser Met Gln Thr Asn
                565                 570                 575

Leu Glu Ile Phe Met Thr Gly Ala Phe Gly Glu Phe Ser Ala Pro Ala
            580                 585                 590

Thr Thr Thr Asp Thr Thr Asn Leu Thr Tyr Asp Lys Phe Gly Tyr Leu
        595                 600                 605

Glu Thr Val Leu Tyr Ser Tyr Ala His Val Glu Glu Ser Thr Glu His
610                 615                 620

Ile Arg Met Tyr Ala Thr Gly Ser Gly Ser Gly Ser Phe Ile Leu Asp
625                 630                 635                 640

Lys Ile Glu Phe Ile Pro Ile Glu Gly Ser Leu Glu Ala Tyr
                645                 650

<210> SEQ ID NO 19
<211> LENGTH: 632
<212> TYPE: PRT
<213> ORGANISM: Bacillus thuringiensis

<400> SEQUENCE: 19

Met Asn Tyr Lys Asp Trp Met Asp Met Cys Thr Arg Gly Glu Ser Gly
```

```
  1               5                   10                  15
Glu Leu Phe Ser Ser Ala Arg Asn Gly Val Ile Ile Ala Thr Gly Ile
                20                  25                  30
Gly Trp Ala Ile Leu Gly Phe Val Pro Val Ile Gly Pro Gly Leu Ser
                35                  40                  45
Ala Ile Ser Gly Leu Leu Asn Val Leu Val Pro Phe Leu Trp Pro Glu
 50                  55                  60
Glu Gln Glu Thr Ser Gln Pro Gln Phe Thr Trp Gln Gln Leu Met Asn
 65                  70                  75                  80
Ala Val Glu Glu Leu Ile Asp Gln Arg Ile Asp Ala Leu Ile Arg Ser
                85                  90                  95
Arg Ala Ile Glu Thr Thr Arg Ile Leu Gln Ser Arg Ile Arg Asp Tyr
                100                 105                 110
Gln Gln Ala Ile Cys Asn Leu Lys Thr Asp Pro Asn Asn Glu Ala Tyr
                115                 120                 125
Lys Ala Asp Val Arg Arg Glu Phe Asn Asp Ala Asp Asp Gln Ala Lys
                130                 135                 140
Ala Ala Ile Ile Gln Phe Asn Pro Arg Asn Pro Asp Gly Thr Glu Asp
145                 150                 155                 160
Ala Lys His Asn Ile Leu Leu Leu Ala Asp Tyr Ala Gln Ala Ala Asn
                165                 170                 175
Val His Leu Leu Leu Leu Arg Asp Val Val Gln Phe Gly Glu Ser Trp
                180                 185                 190
Gly Phe Ser Pro Leu Glu Ile Gln Gln Tyr Tyr Ser Asn Thr Thr Ser
                195                 200                 205
Val Gly Asn Pro Gly Met Leu Gln Leu Leu Ala Asn Tyr Thr Asn His
                210                 215                 220
Cys Val Arg Trp Tyr Asn Ala Gly Leu Ala Thr Phe Asn Ser Tyr Leu
225                 230                 235                 240
Gln Trp Gln Glu Leu Asn Thr Phe Arg Arg Asp Met Thr Ile Met Val
                245                 250                 255
Leu Asp Ile Ala Ser Leu Trp Pro Thr Tyr Asp Pro Lys Ser Tyr Pro
                260                 265                 270
Val Ile Ala Lys Ser Gln Leu Thr Arg Val Leu Tyr Thr Pro Ala Ile
                275                 280                 285
Gly Asn Asp Thr Asp Phe Glu Lys Leu Leu Pro Pro Ser Leu Phe
                290                 295                 300
Ser Trp Leu Arg Glu Ala Ile Phe Tyr Thr Pro Asn Pro Val Tyr Arg
305                 310                 315                 320
Met Glu Tyr Val Lys Tyr Thr Leu Val Leu Gln Lys Thr Leu Ser Asn
                325                 330                 335
Asp Arg Tyr Glu Gln Thr Tyr Gly Ser Asn Phe Gly Ala Asp Ile Ala
                340                 345                 350
Tyr Ser Val Lys Ile Gly Thr Ala Pro Asn Ser Glu Val Tyr Arg Met
                355                 360                 365
His Thr Asn Ala Val Ile Tyr Ser Asn Asp Asn Ala Ser Leu Gly Lys
                370                 375                 380
Ile Thr Phe His Phe Ser Pro Ser Gly Thr Ser Glu Ser Val Gly Arg
385                 390                 395                 400
Glu Ile Val Gly Thr Gly Ile Asp Gln Gly Phe Ala Cys Arg Ser Asn
                405                 410                 415
Leu Asn Glu Pro Cys Asp Pro Cys Val Thr Ala Cys Glu Val Gly Ser
                420                 425                 430
```

```
Val Asn Ala Ser Leu Pro Cys Asp Ser Pro Ser Leu Tyr Ser Glu Arg
        435                 440                 445

Leu Ser Trp Ile Ser Gly Glu Ile Leu Arg Ser Val Asn Phe Ser Ala
    450                 455                 460

Leu Asn Asn Ile Ala Tyr Gly Trp Thr His Val Ser Ala Asp Ala Asn
465                 470                 475                 480

Asn Leu Ile Ser Ala Glu Gln Ile Thr Gln Ile Pro Ala Val Lys Ala
                485                 490                 495

Tyr Glu Leu Ser Gly Asp Ala Leu Val Ile Lys Gly Pro Gly Ser Thr
                500                 505                 510

Gly Gly Asp Leu Val Gln Leu Ser Ser Gly Ala Glu Thr Gly Gln Met
            515                 520                 525

Ala Met Trp Ile Thr Thr Pro Gln Gly Ser His Arg Tyr Arg Val Arg
        530                 535                 540

Ile Arg Tyr Ala Ser Ser Met Gln Thr Asn Leu Glu Ile Phe Met Thr
545                 550                 555                 560

Gly Ala Phe Gly Glu Phe Ser Ala Pro Ala Thr Thr Thr Asp Thr Thr
                565                 570                 575

Asn Leu Thr Tyr Asp Lys Phe Gly Tyr Leu Glu Thr Val Leu Tyr Ser
            580                 585                 590

Tyr Ala His Val Glu Glu Ser Thr Glu His Ile Arg Met Tyr Ala Thr
        595                 600                 605

Gly Ser Gly Ser Gly Ser Phe Ile Leu Asp Lys Ile Glu Phe Ile Pro
    610                 615                 620

Ile Glu Gly Ser Leu Glu Ala Tyr
625                 630

<210> SEQ ID NO 20
<211> LENGTH: 4
<212> TYPE: PRT
<213> ORGANISM: Artificial sequence
<220> FEATURE:
<223> OTHER INFORMATION: endoplasmic reticulum targeting peptide

<400> SEQUENCE: 20

Lys Asp Glu Leu
1
```